United States Patent
Blanco

(10) Patent No.: US 10,076,509 B2
(45) Date of Patent: Sep. 18, 2018

(54) NESTED PARTICLES AND THE USE THEREOF FOR COORDINATED DELVERY OF ACTIVE AGENTS

(71) Applicant: Board of Regents, the University of Texas System, Austin, TX (US)

(72) Inventor: Elvin Blanco, Houston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/144,340

(22) Filed: May 2, 2016

(65) Prior Publication Data
US 2016/0317455 A1 Nov. 3, 2016

Related U.S. Application Data

(60) Provisional application No. 62/155,999, filed on May 1, 2015.

(51) Int. Cl.
| | |
|---|---|
| *A61K 31/337* | (2006.01) |
| *A61K 31/426* | (2006.01) |
| *A61K 9/50* | (2006.01) |
| *A61K 31/343* | (2006.01) |
| *A61K 31/506* | (2006.01) |
| *A61K 31/4439* | (2006.01) |
| *A61K 31/277* | (2006.01) |
| *A61K 9/16* | (2006.01) |
| *A61K 45/06* | (2006.01) |
| *A61K 31/4375* | (2006.01) |
| *A61K 31/704* | (2006.01) |
| *A61K 31/436* | (2006.01) |
| *A61K 47/48* | (2006.01) |

(52) U.S. Cl.
CPC ............ *A61K 31/337* (2013.01); *A61K 9/167* (2013.01); *A61K 9/1647* (2013.01); *A61K 9/5036* (2013.01); *A61K 9/5084* (2013.01); *A61K 31/277* (2013.01); *A61K 31/343* (2013.01); *A61K 31/436* (2013.01); *A61K 31/4375* (2013.01); *A61K 31/4439* (2013.01); *A61K 31/506* (2013.01); *A61K 31/704* (2013.01); *A61K 45/06* (2013.01); *A61K 47/48969* (2013.01)

(58) Field of Classification Search
CPC .. A61K 31/436; A61K 31/343; A61K 31/506; A61K 31/4439; A61K 31/277; A61K 31/337; A61K 31/704; A61K 9/5036; A61K 9/1647; A61K 9/167; A61K 9/5084; A61K 45/06; A61K 2300/00
See application file for complete search history.

(56) References Cited

U.S. PATENT DOCUMENTS

2013/0251640 A1* 9/2013 Tung ................ A61K 47/48238
424/9.6
2014/0017165 A1* 1/2014 Wang .................. A61K 9/5146
424/1.37

OTHER PUBLICATIONS

Elvin Blanco, Sep. 2014 report to the U.S. Army Medical Research and Material Command, Fort Detrick, Maryland, 2014.*
Nafee et al., "Chitosan-coated PLGA nanoparticles for DNA/RNA delivery: effect of the formulation parameters on complexation and transfection of antisense oligonucleotides" in Nanomedicine: Nanotechnology, Biology, and Medicine 3 (2007), 173-183.*
Stephen J. Lippard, Metals in Medicine, Chapter 9, 2004.*
Blanco and Ferrari. "Emerging nanotherapeutic strategies in breast cancer." *The Breast* 23.1 (2014): 10-18.
Blanco et al. "Colocalized delivery of rapamycin and paclitaxel to tumors enhances synergistic targeting of the PI3K/Akt/mTOR pathway." *Molecular Therapy* 22.7 (2014): 1310-1319.
Blanco et al. "Colocalized delivery of rapamycin and paclitaxel to tumors enhances synergistic targeting of the PI3K/Akt/mTOR pathway." *Molecular Therapy* 22.7 (2014): 1310-1319. Supplementary Material.
Blanco et al. "Multistage delivery of chemotherapeutic nanoparticles for breast cancer treatment." *Cancer letters* 334.2 (2013): 245-252.
Danhier et al. "PLGA-based nanoparticles: an overview of biomedical applications." *Journal of controlled release* 161.2 (2012): 505-522.
Deng et al. "Layer-by-layer nanoparticles for systemic codelivery of an anticancer drug and siRNA for potential triple-negative breast cancer treatment" *ACS nano* 7.11 (2013): 9571-9584.
Dong et al. "Doxorubicin and paclitaxel-loaded lipid-based nanoparticles overcome multidrug resistance by inhibiting P-glycoprotein and depleting ATP." *Cancer research* 69.9 (2009): 3918-3926.
Feldman et al. "First-in-man study of CPX-351: a liposomal carrier containing cytarabine and daunorubicin in a fixed 5: 1 molar ratio for the treatment of relapsed and refractory acute myeloid leukemia." *Journal of Clinical Oncology* 29.8 (2011): 979-985.
Hasenstein et al. "Antitumor activity of Triolimus: a novel multidrug-loaded micelle containing Paclitaxel, Rapamycin, and 17-AAG." *Molecular cancer therapeutics* 11.10 (2012): 2233-2242.
Sengupta et al. "Temporal targeting of tumour cells and neovasculature with a nanoscale delivery system." *nature* 436.7050 (2005): 568-572.
Tasciotti et al. "Mesoporous silicon particles as a multistage delivery system for imaging and therapeutic applications." *Nature nanotechnology* 3.3 (2008): 151-157.
Vasir and Labhasetwar. "Biodegradable nanoparticles for cytosolic delivery of therapeutics." *Advanced drug delivery reviews* 59.8 (2007): 718-728.
Wang et al. "Enhanced anti-tumor efficacy by co-delivery of doxorubicin and paclitaxel with amphiphilic methoxy PEG-PLGA copolymer nanoparticies." *Biomaterials* 32.32 (2011): 8281-8290.

* cited by examiner

*Primary Examiner* — Blessing M Fubara
(74) *Attorney, Agent, or Firm* — Parker Highlander PLLC

(57) ABSTRACT

Methods and compositions regarding nested nanoparticles comprising polymer nanoparticles encased in a cyclodextrin shell to facilitate sequence-specific drug release.

23 Claims, 16 Drawing Sheets
(15 of 16 Drawing Sheet(s) Filed in Color)

Thickness of QAβ-CD shell 40.5 nm ± 7.9 nm

NESTED PARTICLES AND THE USE
THEREOF FOR COORDINATED DELVERY
OF ACTIVE AGENTS

CROSS-REFERENCE TO RELATED
APPLICATIONS

This application claims the benefit of U.S. Provisional Patent Application No. 62/155,999, filed May 1, 2015, the entirety of which is incorporated herein by reference.

GOVERNMENT SUPPORT CLAUSE

This invention was made with government support under grant no. W81XWH-11-1-0103 awarded by the United States Department of Defense. The government has certain rights in the invention.

BACKGROUND OF THE INVENTION

1. Field of the Invention

The present invention generally relates to layered particle compositions and methods for controlled drug delivery and the use thereof for prevention and treatment of pathological conditions, such as cancer.

2. Description of Related Art

Combination chemotherapy represents a mainstay treatment modality essential for improvement of survival rates in many cancers as well as other disease conditions. However, despite numerous regimens employed clinically, patient responses following combination therapies, such as polychemotherapy, often remains dismal. Recent molecular insights into underlying signaling pathways and networks suggest that drug synergy in combination chemotherapy may be significantly enhanced if the order of administration, scheduling, and dose duration are given proper consideration.

However, while specific combinations of drugs delivered in a time-staggered fashion have been shown to synergistically enhance cell killing pre-clinically (e.g., in cell culture systems), this strategy has not translated successfully to the clinic. Pharmacokinetic limitations of conventional drug formulations, including short circulation half-lives and heightened volumes of distribution, result in non-specific accumulation of drugs in healthy tissues and insufficient bioavailability in tumors. Moreover, different routes of administration, as well as distinct excipients associated with individual formulations of conventional drugs, result in disparate pharmacokinetic parameters that preclude adherence to strict time constraints specifically in tumors, thereby negating therapeutic crosstalk between synergistic agents. Thus, there remains a need for methods (and delivery systems) that can provide sequenced and timed delivery of combinations of different therapeutic or imaging agents.

SUMMARY OF THE INVENTION

In a first embodiment the invention provides a particle comprising (i) a charged core element and a first active agent embedded in, or conjugated to, the core element; and (ii) a cyclodextrin coating, surrounding the core element, said coating having the opposite charge of the core element and comprising a second active agent. In some aspects, the first active agent or the second active agent is a therapeutic agent. In other aspects, the first active agent or the second active agent is an imaging agent. In certain aspects, the first active agent and the second active agent are therapeutic agents. In further aspects, the charged core element comprises a negatively charged group and the cyclodextrin coating comprises a positively charged group. In other aspects, the charged core element comprises a positively charged group and the cyclodextrin coating comprises a negatively charged group. As used herein, a positively or negatively charged group can, in some aspects, refer to groups having a partial positive or negative charge.

In some aspects, the cyclodextrin comprises β-cyclodextrin, α-cyclodextrin or γ-cyclodextrin. In certain aspects, the cyclodextrin comprises a negatively charged group, such as a phosphate, carboxylate, sulfate or nitrate group. In particular aspects, the cyclodextrin comprises a positively charged group. The positively charged group may be an ammonium, a guanidinium, histidine or other nitrogen-containing heteroaryl groups. In specific aspects, the cyclodextrin comprises ammonium β-cyclodextrin. In still further aspects, a particle of the embodiments can be characterized by the average thickness of the cyclodextrin layer. For example, the particle may comprise a cyclodextrin layer that has an average thickness of 5 to 100 nm, 10 to 100 nm, 20 to 60 nm, 30 to 50 nm, 35 to 45 nm or about 40 nm. In still further aspects, the cyclodextrin layer can be defined by the average half life of the layer when exposed to an aqueous solution such as saline or serum. For example, in some aspects a particle of the embodiments has a cyclodextrin layer with a half-life of about or at least about 2, 4, 6, 8, 10, 12, 14, 16, 18, 20, 22 or 24 hours when exposed to serum.

In certain aspects, the charged core element comprises a negatively charged group, such as a phosphate, carboxylate, sulfate or nitrate group. In further aspects, the core element comprises a positively charged group, such as an ammonium, a guanidinium, histidine or other nitrogen-containing heteroaryl group. In certain aspects, the core element comprises a metal or metal oxide particle. In other aspects, the charged core element comprises a quantum dot or a PLGA particle. In further aspects, the core element comprises a negatively charged PLGA particle. In still further aspects, the charged core element is characterized by its average diameter. For example, the core element may an average diameter of 5 to 1000 nm, 10 to 500 nm, 20 to 200 nm, 20 to 100 nm, 50 to 100 nm or about 70 nm.

In some aspects, a particle of the embodiments, comprising both the inner core and the cyclodextrin layer, has a diameter of between about 10 and 1,000 nm. In specific aspects, the particle has a diameter of between about 50 and 500 nm or about 100 and 200 nm. In certain specific aspects, the particle has an average diameter of 120-180 nm.

Thus, a specific embodiment, there is provided a particle comprising a negatively charged PLGA core element having a first active agent embedded therein and a positively charged cyclodextrin (e.g., ammonium 3-cyclodextrin) coating surrounding the core element, said coating comprising a second active agent.

In yet still a further embodiment there is provided a composition comprising a population of particles in accordance with the embodiments. In certain aspects, the composition comprises $10^3$ to $10^{16}$, $10^4$ to $10^{15}$, $10^5$ to $10^{14}$, $10^6$ to $10^{14}$, $10^6$ to $10^{15}$ or $10^6$ to $10^{16}$ particles. In some aspects, the particles are comprised in a pharmaceutically acceptable carrier. In still further aspects, the particles may, themselves be encapsulated in a coating, such as a pill or capsule. In certain aspects, a coating for use in encapsulating particles is a dissolvable coating.

In certain aspects, the first and/or second active agent is a therapeutic agent. In some cases the first and second agent are different therapeutic agents. However, in certain aspects, the first and second therapeutic agents are the same agent. In some aspects, the second active agent can be released quickly, to provide immediate therapeutic effect, and the first agent can be released in a delayed or prolonged method, to provide a delayed or prolonged therapeutic effect.

In specific aspects, the second active agent is an Akt kinase inhibitor and the first active agent is an mTOR inhibitor. In further aspects, the Akt inhibitor comprises Paclitaxel or MK-2206. In some aspects, the mTOR inhibitor comprises Rapamycin. In other aspects, the second active agent is an antibody and the first active agent is a chemotherapeutic. In particular aspects, the second active agent is an ERK inhibitor and the first active agent is a RAF inhibitor. ERK inhibitor may comprise SCH772984. The RAF inhibitor may comprise GDC-0879.

In still further aspects, the first active agent is a chemotherapeutic and the second active agent is a drug efflux pump inhibitor. In certain aspects, the drug efflux pump inhibitor is P-glycoprotein 1 (P-gP) inhibitor. The P-gP inhibitor may comprise Verapamil. In other aspects, the chemotherapeutic comprises doxorubicin or paclitaxel.

In further aspects, the first and/or second active agent of a particle of the embodiments comprises an antiarrhythmic agent. In some aspects, both the first and second active agents comprise antiarrhythmic agents (e.g., the same agent). In some aspects, the antiarrhythmic agent is a beta-blocker, a $Ca^{2+}$ channel blocker, a $K^+$ channel blocker or a $Na^+$ channel blocker. Examples of such antiarrhythmic agents include, without limitation, Quinidine, Ajmaline, Procainamide, Disopyramide, Lidocaine, Phenytoin, Mexiletine, Tocainide, Encainide, Flecainide, Propafenone, Moricizine, Carvedilol, Propranolol, Esmolol, Timolol, Metoprolol, Atenolol, Bisoprolol, Amiodarone, Sotalol, Ibutilide, Dofetilide, Dronedarone, E-4031, Verapamil, Diltiazem, Adenosine and/or Digoxin.

In certain aspects, the particle may further comprise a surface stabilizer and/or targeting agent. Non-limiting examples of surface stabilizer include citrate, polyacetylene glycol, cysteine, folic acid, polypropylene glycol, copolymers of polyethylene glycol and polypropylene glycol, polylysine, polyvinyl alcohol, human serum albumin, bovine serum albumin, hyaluronic acid, polyethyleimine (PEI) or polyvinylprrolidone (PVP). For example, the polyacetylene glycol is polyethylene glycol (PEG). The polyethylene glycol may have a molecular weight ranging from 500-20,000 dalton, or more particularly, from 1000-5000 dalton. For example, the PEG may have at least, at most or about 100, 200, 300, 400, 500, 600, 700, 800, 900, 1000, 2000, 3000, 4000, 5000, 6000, 7000, 8000, 9000, 10,000, 20,000, 30,000, 40,000, 50,000 dalton, or any range derivable therefrom. In some aspects, the surface stabilizer can also act as a targeting agent (e.g., hyaluronic acid and folic acid can be used to target particular classes of tumor cells).

In certain aspects, the particle may be formulated in a pharmaceutically acceptable particle composition. The particle formulation can be a liquid formulation or a solid formulation, such as a powder. Particularly, the composition may be dehydrated or lyophilized for long term storage with improved stability. Alternatively, the composition may be present in a substantially aqueous solution. The composition may be rehydrated or re-suspended in a solution or liquid from the previously lyophilized composition. The composition used in the methods may be previously dehydrated, lyophilized or in some other aspects, an aqueous solution or liquid formulation of previously lyophilized or dehydrated composition, an effective amount of which are administered to the subject. The present invention also provides, in certain aspects, previously lyophilized or dried composition after being stored at 4 degree for at least 1 week, for at least 3 weeks, for up to 4 weeks, or any period derivable therein, for treating the disease with retained activity after resuspension or rehydration.

In still a further embodiment the invention provides a method of treating a subject comprising administering a composition as described above to a subject in need of the treatment. In particular aspects, the method is additionally defined as a method of imaging a subject. In other aspects, the method is additionally defined as a method of treating a disease in a subject. In specific aspects the disease may be cancer, an infectious disease or an autoimmune disease.

For a safe and effective dosage, the particle or particle formulation may be administered at a dose of at least, at most or about $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $2 \times 10^{14}$, $3 \times 10^{14}$, $4 \times 10^{14}$, $5 \times 10^{14}$, $8 \times 10^{14}$, $1 \times 10^{15}$, $1 \times 10^{16}$, $1 \times 10^{17}$, $1 \times 10^{18}$, $1 \times 10^{19}$, $1 \times 10^{20}$ particles or any intermediate range per kg body weight or per tumor. In certain aspects, the particle or particle formulation may be administered in a dose of about 500 $mg/m^2$ (body surface)/day, about 10 to about 300 $mg/m^2$/day, 20 to about 200 $mg/m^2$/day, about 30 to about 200 $mg/m^2$/day, about 40 to about 100 $mg/m^2$/day, about 50 to about 100 $mg/m^2$/day or any range derivable therein to a subject such as a human.

The particle or particle formulation may be administered intravenously, intradermally, intraarterially, intraperitoneally, intralesionally, intracranially, intraarticularly, intraprostaticaly, intrapleurally, intratracheally, intravitreally, intravaginally, intrarectally, intratumorally, intramuscularly, intraperitoneally, subcutaneously, subconjunctival, intravesicularily, mucosally, intrapericardially, intraumbilically, intraocularally, intrathecally, locally, by injection, by infusion, by continuous infusion, by localized perfusion bathing target cells directly, via a catheter, or via a lavage. For example, the composition may be administered by injection or infusion.

To have a better therapeutic benefit, a particle or particle formulation of the embodiments may be administered in combination with at least an additional agent such as a radiotherapeutic agent, a hormonal therapy agent, an immunotherapeutic agent, a chemotherapeutic agent, a cryotherapeutic agent and/or a gene therapy agent.

In some embodiments, cancer cells may be treated by methods and compositions of the embodiments. In some aspects, the particles of these compositions comprise paclitaxel as the second active agent and rapamycin as the first active agent. In other aspects, the particles may comprise MK-2206 as the second active agent and rapamycin as the first active agent. In further aspects, the particles of these compositions may comprise SCH772984 as the second active agent and GDC-0879 as the first active agent.

In other embodiments, the methods and compositions of the invention may assist in overcoming multidrug resistance mechanisms in cancer and other disease states. This would involve targeting of drug efflux pumps (e.g. P-gP). In some aspects, the particles of the compositions comprise verapamil as the second active agent and doxorubicin or paclitaxel first active agent.

In further embodiments, cardiovascular disease, such as pulmonary hypertension, heart failure, and restenosis, may be treated by the methods and compositions of the embodiments. The particles of these compositions may comprise angiotensin receptor blockers, LY294002, MK-2206, and/or rapamycin. In some aspects, the LY294002 or MK-2206 is the second active agent and rapamycin is the first active agent.

In still further aspects, particles of the embodiments can be used to treat cardiac arrhythmia. In this case, the first and/or second active agent may be an antiarrhythmic agent such as amiodarone.

In still further embodiments, parasitic infections may be treated by the methods and compositions of the embodiments. In certain aspects, the particles of these compositions may comprise eflornithine as the second active agent and praziquantel as the first active agent.

In yet still further embodiments, the subjects in need of treatment may be organ transplant recipients. In particular aspects, the subjects may be treated with compositions comprising particles comprising an mTOR inhibitor (e.g., tacrolimus) as the second active agent and dexamethasone as the first active agent.

In still yet a further embodiment, the particle may additionally comprise a further (third) layer or coating (e.g., an additional layer of cyclodextrin) surrounding the cyclodextrin coating. In some aspects, the additional layer comprises a third active agent. In still more embodiments, the particle may be further layered with still further coatings (e.g. a fourth, fifth, sixth or more layer). In some aspects, the additional coatings comprise additional active agents. In certain aspects, the agents may be time-released to provide sequential therapy to a subject. In some aspects, the sequential delivery of agents may target particular pathways in the subject. For example, the PI3k/Akt/mTOR and MAPK/ERK pathways, or the PI3k/Akt/mTOR and p53 pathway.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

DETAILED DESCRIPTION OF ILLUSTRATIVE EMBODIMENTS

Figure 1:
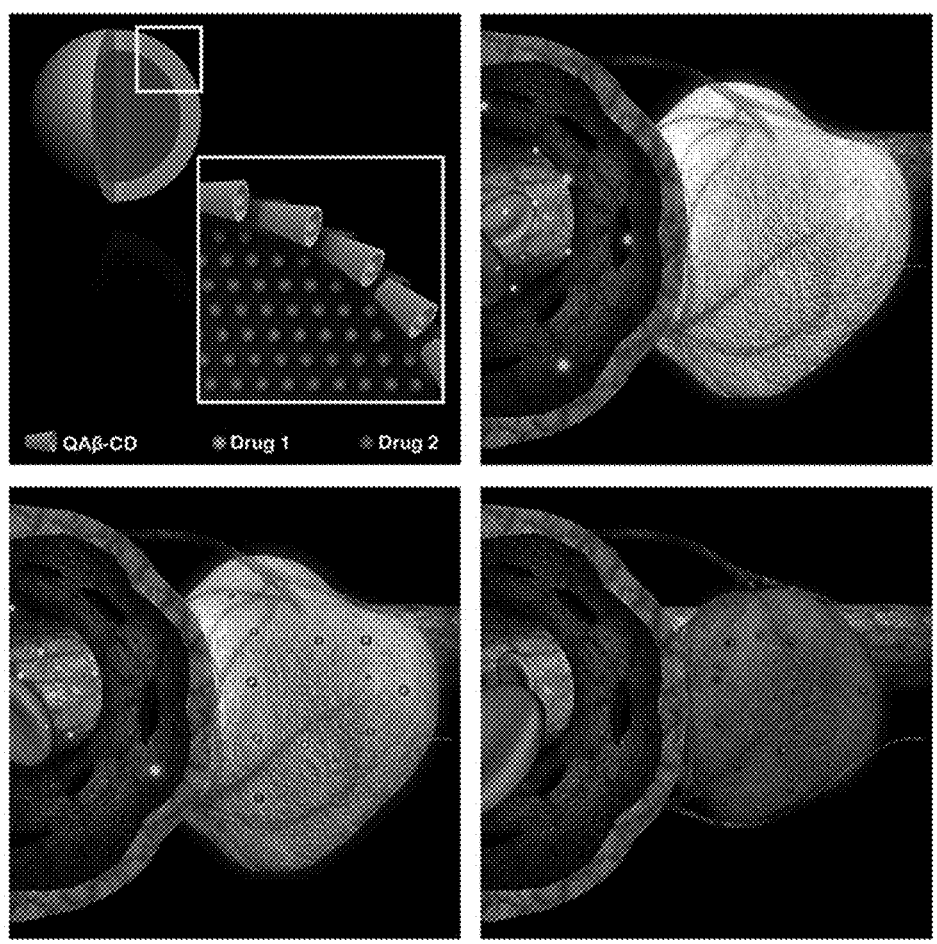
FIG. 1. Illustrates nested nanoparticles designed for time and sequential release of synergistic therapeutics site-specifically in tumors. The platform comprises drug-containing PLGA nanoparticles with an outer shell composed of drug complexed with cyclodextrin (QAβ-CD). Following intravenous administration, nanoparticles may accumulate in tumors through the enhanced permeability and retention (EPR) effect. Once at the site, drug (e.g., a second active agent) in the outer shell is released during the early timepoints, chemosensitizing cancer cells to a second drug (e.g., a first active agent) released at later timepoints from the nanoparticle core, resulting in synergistic enhancement of tumor cell killing.

Combination administration of biologically active agents offers a potentially powerful method for treatment (or imaging) of diseased tissues. However, difference is drug formulation, routes of administration and pharmacokinetics among other issues have thus far limited the applicability of such combination therapies. Described herein, is a novel particle platform capable of releasing combinations of agents in a time- and sequence-dependent manner. In particular, it was discovered that by forming active agents into distinct layers of a particle delivery platform the sequence and timing or delivery could be precisely controlled. Moreover by forming the particle layers with polymers have opposing charge, highly stable formulations could be achieved. In particular, particles comprise a drug-containing (e.g., polymeric) core, surrounded by an outer shell composed of drug complexed to charged cyclodextrin.

The particles and methodologies provided herein open new highly active methods for therapy. For example, by delivering agents in a time- and sequence-dependent manner, apoptotic pathways can be exploited by use of one drug that chemosensitizes cancer cells to a second drug provided in the particle core. Moreover, methods where agents are delivered sequentially may also serve to inhibit feedback loops and survival mechanisms inherent to complex signaling cascades by targeting multiple components along the same pathway. By way of example, but not limitation, the nested nanoparticles, can also be used for sequential delivery of drugs that can target crosstalk activation among pathways, such as but not limited to the PI3k/Akt/mTOR and MAPK/ERK pathways, or the PI3k/Akt/mTOR and p53 pathway. More specifically, the incorporation of the MDM2 inhibitor RITA, which results in increased p53 expression in combination with an inhibitor of the PI3k/Akt/mTOR pathway (e.g. rapamycin, PI-103) can provide such sequential therapy. An additional example includes the drug GDC-0994, an ERK inhibitor, which could be combined with an inhibitor of the PI3k/Akt/mTOR pathway (e.g. rapamycin, PI-103) for sequential therapy.

I. PARTICLES OF THE EMBODIMENTS

Active agents for use in particles of the embodiments can comprise imaging agents or therapeutic agents. For example, the imagining agent can be component used in MRI, PET, SPECT, CT, or photoacoustic tomography. In some aspects, the imaging agent is a radionuclide or a dye. In further aspects, the active agent is a therapeutic active agent such as an inhibitory nucleic acid (e.g., a siRNA), a nucleic acid vector, a small molecule, an antibody, or a polypeptide.

For example, in some aspects, a first or second (or further) active agent may be is a protein kinase inhibitor such as a EGFR, VEGFR, AKT, Erb1, Erb2, ErbB, Syk, Bcr-Abl, JAK, Src, GSK-3, PI3K, Ras, Raf, MAPK, MAPKK, mTOR, c-Kit, eph receptor or BRAF inhibitor. Nonlimiting examples of protein kinase inhibitors include Afatinib, Axitinib, Bevacizumab, Bosutinib, Cetuximab, Crizotinib, Dasatinib, Erlotinib, Fostamatinib, Gefitinib, Imatinib, Lapatinib, Lenvatinib, Mubritinib, Nilotinib, Panitumumab, Pazopanib, Pegaptanib, Ranibizumab, Ruxolitinib, Saracatinib, Sorafenib, Sunitinib, Trastuzumab, Vandetanib, AP23451, Vemurafenib, MK-2206, GSK690693, A-443654, VQD-002, Miltefosine, Perifosine, CAL101, PX-866, LY294002, rapamycin, temsirolimus, everolimus, ridaforolimus, Alvocidib, Genistein, Selumetinib, AZD-6244, Vatalanib, P1446A-05, AG-024322, ZD1839, P276-00, and GW572016.

In certain aspects, a first or second (or further) active agent may be a chemotherapeutic agent. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristine, vinblastine and methotrexate and pharmaceutically acceptable salts, acids or derivatives of any of the above.

Further more a first or second (or further) active agent may be an anti-hormonal agent that acts to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene; aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor and a HER2 expression inhibitor and pharmaceutically acceptable salts, acids or derivatives of any of the above.

Active Agent Incorporation

As detailed herein in some aspects, an active agent can be embedded in the inner core or cyclodextrin layer of a particle of the embodiments. For example, PLGA core structures can be formulated with one or more incorporated active agents using emulsion techniques such as those detailed in Stigliano et al., 2013, which is incorporated herein by reference. Likewise, cyclodextrin layers can be applied to particles in the presence of one or more active agents to provide a layer with an embedded active agent. Additionally, any other linking/coupling agents and/or mechanisms known to those of skill in the art can be used to combine active agents with particles of the embodiments. For example, antibody-antigen interaction, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, bispecific antibodies and antibody fragments, or combinations thereof.

Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane. The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

Targeting of Particles

Targeted delivery of particles of the embodiments can be achieved by the addition of ligands (e.g., to the surface of the particle) without compromising the ability of nanoparticles to deliver their loads. It is contemplated that this may enable more specific delivery to target cells, tissues and organs. The targeting specificity of the ligand-based delivery systems is based on the distribution of the ligand receptors on different cell types. It is preferable that the ligand to be conjugated to the nanoparticles may bind to the receptors that specifically or predominantly express in tumor cells so that the nanoparticle may be preferentially delivered to the tumor cells. For example, specific antibodies such as anti-CD20 (Rituximab) may be conjugated to the nanoparticles to deliver nanoparticles to malignant B-cells such as those of chronic lymphocytic leukemia and B-cell lymphoma.

The targeting ligand may either be non-covalently or covalently associated with a nanoparticle, and can be conjugated to the nanoparticles by a variety of methods as discussed herein. Examples of proteins or peptides that can be used to target nanoparticles include transferin, lactoferrin, TGF-α, nerve growth factor, albumin, HIV Tat peptide, RGD peptide, and insulin, as well as others (Gupta et al., 2005; Ferrari, 2005).

In further aspects, the particle may be coupled to a tumor targeting moeity. In certain embodiments the tumor targeting moiety is an antibody that binds an antigen selected from the group consisting of, a gastrointestinal cancer cell surface antigen, a lung cancer cell surface antigen, a brain tumor cell surface antigen, a glioma cell surface antigen, a breast cancer cell surface antigen, an esophageal cancer cell surface antigen, a common epithelial cancer cell surface antigen, a common sarcoma cell surface antigen, an osteosarcoma cell surface antigen, a fibrosarcoma cell surface antigen, a melanoma cell surface antigen, a gastric cancer cell surface antigen, a pancreatic cancer cell surface antigen, a colorectal cancer cell surface antigen, a urinary bladder cancer cell surface antigen, a prostatic cancer cell surface antigen, a renal cancer cell surface antigen, an ovarian cancer cell surface antigen, a testicular cancer cell surface antigen, an endometrial cancer cell surface antigen, a cervical cancer cell surface antigen, a Hodgkin's disease cell surface antigen, a lymphoma cell surface antigen, a leukemic cell surface antigen and a trophoblastic tumor cell surface antigen.

In particular embodiments, the tumor targeting moiety is an antibody or ligand that binds an antigen or a receptor selected from the group consisting of 5 alpha reductase, α-fetoprotein, AM-1, APC, APRIL, BAGE, β-catenin, Bc12, bcr-abl (b3a2), CA-125, CASP-8/FLICE, Cathepsins, CD19, CD20, CD21, CD23, CD22, CD38, CD33, CD35, CD44, CD45, CD46, CD5, CD52, CD55, CD59 (791Tgp72), CDC27, CDK4, CEA, c-myc, Cox-2, DCC, DcR3, E6/E7, EGFR, EMBP, Ena78, FGF8b and FGF8a, FLK-1/KDR, Folic Acid Receptor, G250, GAGE-Family, gastrin 17, GD2/GD3/GM2, GnRH, GnTV, gp100/Pme117, gp-100-in4, gp15, gp75/TRP-1, hCG, Heparanase, Her2/neu, HERS, Her4, HMTV, HLA-DRIO, Hsp70, hTERT, IGFRI, IL-13R, iNOS, Ki 67, KIAA0205, K-ras, H-ras, N-ras, KSA, (C017-1A), LDLR-FUT, MAGE Family (MAGE1, MAGE3, etc.), Mammaglobin, MAP17, Melan-A/, MART-1, mesothelin, MIC A/B, MT-MMP's, such as MMP2, MMP3, MMPI, MMP9, Mox1, MUC-1, MUC-2, MUC-3, and MUC-4, MUM-1, NY-ESO-1, Osteonectin, p15, P170/MDRI, p53, p97/melanotransferrin, PAI-1, PDGF, Plasminogen (uPA), PRAME, Probasin, Progenipoietin, PSA, PSM, RAGE-1, Rb, RCAS1, SART-1, SSX gene, family, STAT3, STn, TAG-72, TGF-α, TGF-β, and Thymosin 015, nucleolin, Ca15-3, astro Intestinal Tumor Antigen (Ca19-9), ovarian Tumor Antigen (Ca125), Tag72-4 Antigen (CA72-4) and carcinoembryonic antigen (CEA). In a particular example, the targeting ligand may be a CD44 binding ligand, such as hyaluronic acid (HA).

II. METHODS OF TREATMENT

In some embodiments, an effective amount of drug-loaded particles of the embodiments are administered to a subject. A skilled artisan readily recognizes that, in many cases, particles of the embodiments may not provide a cure but may only provide partial benefit, such as alleviation or improvement of at least one symptom. The particle compositions of the embodiments may be administered to a subject in the form of a pharmaceutical composition for the treatment of, for example, cancer, autoimmunity, transplantation rejection, post-traumatic immune responses, cardiovascular disease, and infectious diseases. More specifically, the particles of the embodiments may be useful in eliminating cells involved in immune cell-mediated disorder, including lymphoma; autoimmunity, transplantation rejection, graft-versus-host disease, ischemia and stroke. Pharmaceutical compositions comprising the particles of the embodiments may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations which can be used pharmaceutically. Proper formulation is dependent upon the route of administration chosen.

In certain embodiments, cancer cells may be treated by methods and compositions of the embodiments. Cancers that may be treated with the particles of the embodiments include but are not limited to cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In preferred embodiments systemic formulations of the particles of the embodiments are contemplated. Systemic formulations include those designed for administration by injection, e.g. subcutaneous, intravenous, intramuscular, intrathecal or intraperitoneal injection, as well as those designed for transdermal, transmucosal, inhalation, oral or pulmonary administration. In some aspects, the particles of the embodiments are delivered by direct intravenous or intratumoral injection.

For injection, the particles of the embodiments may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the particles may be in powder form for constitution with a suitable vehicle, e.g., sterile pyrogen-free water, before use.

Effective Dosages

The particles of the embodiments will generally be used in an amount effective to achieve the intended purpose. For systemic administration, a therapeutically effective dose can be estimated initially from in vitro assays. For example, a dose can be formulated in animal models to achieve a circulating concentration range that includes the IC50 as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the molecules which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day.

In cases of local administration or selective uptake, the effective local concentration of the particles may not be related to plasma concentration. One having skill in the art will be able to optimize therapeutically effective local dosages without undue experimentation.

The amount of particles administered will, of course, be dependent on the subject being treated, on the subject's weight, the severity of the affliction, the manner of administration and the judgment of the prescribing physician.

Toxicity

Preferably, a therapeutically effective dose of the particles of the embodiments will provide therapeutic benefit without causing substantial toxicity. Toxicity of the particles described herein can be determined by standard pharmaceutical procedures in cell cultures (see, e.g., FIG. 10) or experimental animals, e.g., by determining the LD50 (the dose lethal to 50% of the population) or the LD100 (the dose lethal to 100% of the population). The dose ratio between toxic and therapeutic effect is the therapeutic index. The data obtained from these cell culture assays and animal studies can be used in formulating a dosage range that is not toxic for use in human. The dosage may vary within this range depending upon the drug combination of the particles and the route of administration utilized. The exact formulation, route of administration and dosage can be chosen by the individual physician in view of the patient's condition.

III. DEFINITIONS

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

In this disclosure, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements and components comprising one unit and elements or components that comprise more than one unit unless specifically stated otherwise.

Throughout this application, the term "about" is used to indicate that a value includes the inherent variation of error for the device, the method being employed to determine the value, or the variation that exists among the study subjects.

As used herein, and unless otherwise indicated, the terms "treat," "treating," "treatment" and "therapy" contemplate an action that occurs while a patient is suffering from a disorder that involves a disease or disorder, such as but not limited to cancer, autoimmune disease, infectious disease, congenital disease, cardiovascular disease or neurological disease. Treating refers to reducing the severity of one or more symptoms or effect of such a disorder.

As used herein, and unless otherwise indicated, the terms "prevent," "preventing," and "prevention" contemplate an action that occurs before a patient begins to suffer from a disorder that involves a disease or disorder such as but not limited to cancer, autoimmune disease, infectious disease, congenital disease, cardiovascular disease or neurological disease. Thus preventing refers to method or composition that delays the onset of, and/or inhibits or reduces the severity of a disease or disorder.

As used herein, and unless otherwise specified, a "therapeutically effective amount" of a compound is an amount sufficient to provide any therapeutic benefit in the treatment or management of a disease or disorder. Thus, a therapeutically effective amount of a compound means an amount of the compound, alone or in combination with one or more other compounds or therapies and/or therapeutic agents that provide any therapeutic benefit in the treatment or management of a disease or disorder.

As used herein, "patient" or "subject" includes mammalian organisms which are capable of suffering from a disease or disorder, such as human and non-human mammals. For example, a subject can include, but is not limited to, rodents, mice, rats, non-human primates, companion animals such as dogs and cats as well as livestock, e.g., sheep, cow, horses, etc.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—General Methods and Results

Materials:

Poly(DL-lactide-co-glycolide) 50:50 (PLGA, inherent viscosity 0.95-1.20) was purchased from Durect® Corporation (Birmingham, Ala., USA). Quaternary ammonium β-cyclodextrin (QAβ-CD) was purchased from Cyclodextrin Technologies Development, Inc. (Alachua, Fla.). Rhodamine ($\lambda$ex 554 nm; $\lambda$em 627 nm) was purchased from and Sigma Aldrich (St. Louis, Mo., USA). The fluorescent probe 6-(((4,4-Difluoro-5-(2-Thienyl)-4-Bora-3a,4a-Diaza-s-Indacene-3-yl) styryloxy) acetyl) aminohexanoic Acid, Succinimidyl Ester) (Bodipy; $\lambda$ex of 630 nm, $\lambda$em of 650 nm) was purchased from Life Technologies (Grand Island, N.Y., USA). MCF-7 human breast cancer cells were obtained from the American Tissue Culture Collection (Manassas, Va., USA). Human primary endothelial cells were obtained from Promega (Madison, Wis., USA). Cell lines were cultured in Dulbecco's modified Eagle's medium (DMEM)/F-12 (Mediatech, Inc., Manassas, Va., USA) supplemented with 10% (v/v) FBS (Sigma Aldrich, St. Louis, Mo., USA) and maintained at 37° C. in a humidified atmosphere containing 5% CO2 throughout the course of experimentation.

Adhesive Interaction Between PLGA Nanoparticles and Cyclodextrin:

Adhesion force between QAβ-CD and PLGA was examined via AFM using a MultiMode 8 AFM (Bruker, Madison, Wis., USA). Chemical modifications of QAβ-CD functionalized AFM tips and PLGA nanoparticle fixed substrates for force measurements are described in Supporting Information. Force spectroscopy measurements were conducted in liquid conditions with DI water as a buffer. Sensitivity and spring constants for the cantilever were calibrated automatically from a stable force curve. The functionalized AFM tip was manually placed over a PLGA nanoparticle film substrate to ensure an interaction between the QAβ-CD-functionalized tip and PLGA, as visualized via AFM microscopy. When the tip was in contact with the PLGA nanoparticle surface, the tip ramp model was activated, and force curves were automatically recorded on a specific spot of the PLGA surface. To confirm the reproducibility of the force curves, at least 5 spots on the PLGA nanoparticles were selected randomly.

Fabrication and Characterization of Core-Forming PLGA Nanoparticles:

PLGA nanoparticles were fabricated using a modified double emulsion procedure (Stigliano et al., 2013). Resulting nanoparticles were characterized for size and surface charge using a Malvern Zetasizer Nano ZS dynamic light scattering (DLS) instrument (Malvern Instruments Ltd, Worcestershire, UK). Size and morphology were verified using SEM (Nova NanoSEM™ 230, FEI, Hillsboro, Oreg., USA) and AFM. Encapsulation of rhodamine within nanoparticles was examined using a Synergy H4 Hybrid Reader at $\lambda max=554$ nm.

Bodipy Complexation with QAB-CD:

Bodipy was dissolved in THF, and added to a QAβ-CD aqueous solution. After stirring of the mixture for 4 h, THF was allowed to evaporate overnight. The resulting suspension was centrifuged at 10,000 rpm for 5 min and filtered using a 0.45 μm filter. The concentration of bodipy following complexation with cyclodextrin was determined as described above at a $\lambda max=630$ nm.

Fabrication and Characterization of Nested Nanoparticles:

Rhodamine-containing PLGA nanoparticles were incubated with bodipy•QAβ-CD complexes in solution. Following 3 h, nanoparticles were washed to remove excess bodipy•QAβ-CD. Nanoparticles were then characterized via DLS, SEM, and AFM, as described previously. The ratio of PLGA to cyclodextrin in the platform was determined following dissolution of nested nanoparticles in dichloromethane and water, so as to obtain phase separation of the constituent components, respectively. Following evaporation, component parts were weighed. Confocal microscopy was performed at predetermined timepoints to examine the architecture of the nested nanoparticles. Briefly, nested nanoparticles were mounted onto a microscope slide for fluorescence examination using an upright inverted Nikon A1 confocal microscope (Nikon Instruments, Melville, N.Y., USA), equipped with a 20× and 60× oil-immersion objective. Nikon Elements v4.1 software (Nikon Instruments, Melville, N.Y., USA) was used for image processing.

Release Kinetics from Nested Nanoparticles:

Fluorophore release was determined according to a previously published procedure (Woodrow et al., 2009). Absorbance of bodipy and rhodamine were detected using the Synergy H4 Hybrid Reader as described above. In a separate study, nanoparticles were centrifuged at predetermined timepoints, resuspended in water, and the surface charge determined via zeta potential analysis, as described above.

Cytotoxicity of Nested Nanoparticles:

Cytotoxicity was determined via MTT assay using a CellTiter 96® Assay (Promega Corp., Madison, Wis., USA). Briefly, 10,000 human primary endothelial cells were seeded onto a 96-well plate. After 24 h, cells were treated with increasing doses of PLGA nanoparticles and nested nanoparticles. Plates were then incubated at 37° C. for 24 h in CO2 incubator. After incubation, the cells were carefully washed 3 times with PBS. Dye Solution was added to all the wells and incubated 4 h. After incubation, Solubilization Solution/Stop Mix was added to all wells followed by overnight incubation at 4° C. Readings were taken using an Infinite 200 Pro plate reader (Tecan, Männedorf, CH) at wavelengths of 570 nm (reference wavelength 650 nm).

Nested Nanoparticle Internalization and Intracellular Release Following Incubation with MCF-7 Breast Cancer Cells:

MCF-7 cells were seeded and kept in culture until 50% confluency. Cells were then incubated with nanoparticles, and at predetermined timepoints, samples were fixed with 4% methanol-free paraformaldehyde and permeabilized with 0.1% Triton-X 100 in PBS. Cells were washed, and stained with a solution containing 0.5 unit μl-1 of Alexa Fluor 555-conjugated phallodin (Molecular Probes, Life Technologies, Grand Island, N.Y., USA) at RT. Nuclei were stained with Vectashield mounting media with DAPI (Vector Laboratories, Burlingame, Calif., USA). Slides were mounted and examined via confocal microscopy as described above.

For experiments involving flow cytometry analysis, cells were seeded and 24 h later incubated with nanoparticles. At predetermined timepoints, cells were collected, fixed, and resuspended in PBS. Fluorescence within cells was determined by side scatter measurements using a BD LSR-Fortessa Flow Cytometer (BD Biosciences, San Jose, Calif., USA), equipped with a 561 and 630 nm laser. BD FACSDiva software (BD Biosciences, San Jose, Calif., USA) was used for acquisition and data analysis.

In Vivo Accumulation and Release of Nested Nanoparticles in Breast Tumors:

MCF-7 cells ($5 \times 10^6$) were inoculated in the mammary fat pads of 4- to 6-week-old female nu/nu mice. Mice were implanted with 17β-estradiol pellets subcutaneously. Nanoparticles were administered intravenously and at predetermined timepoints, the mouse was sacrificed and the tumor harvested. Tumor tissues were frozen and sectioned into 7 μm tissue slices using an HM 550 Cryostat (Thermo Fischer Scientific, Waltham, Mass., USA). Tissues were fixed and stained with 4% methanol-free paraformaldehyde for 20 min. Following fixation, samples were washed with PBS. Slides were mounted and tissues imaged using confocal microscopy as previously described. The presence of fluorescence over time, surface intensity plots, and area fraction of the tissue sections were examined using Nikon Elements v4.1 software. For area fraction analysis, the fluorescence emitted by bodipy and rhodamine was obtained from 4 sections from different regions of the tumor (n=3). A ratiometric percentage of area fractions of both fluorophores were extracted from the total area of the image.

Statistical Analysis:

All results comprise means, while error bars represent standard deviations. Statistics were calculated using GraphPad Prism software. Comparison between two groups was determined using one-way ANOVA followed by F-test, where $p<0.01$ was significant.

Example 2—Examination of Adhesion Force Between QAB-CC and PLGA

Figure 2:
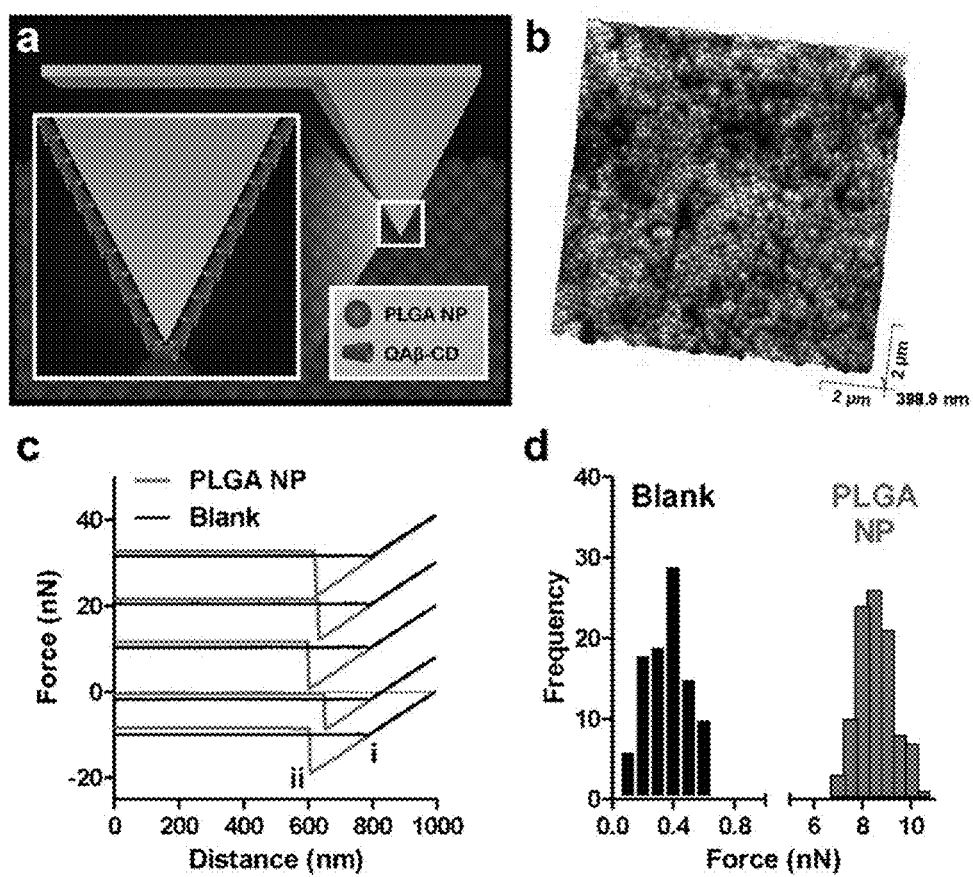
FIGS. 2A-D. Illustrates atomic force microscopy (AFM) examination of adhesive force between QAβ-CD and PLGA. 2A. Schematic illustrating the QA-CD-functionalized AFM tip and PLGA nanoparticles settled on the substrate. 2B. AFM topographical image of PLGA nanoparticles. 2C. Representative attractive F-D curves of positive QAβ-CD interacting with the negative PLGA surface. Gray and black traces indicate retraction (detachment) signals of the AFM tip from a PLGA nanoparticle substrate and blank substrate, respectively. The five different force curves were produced from the same QAβ-CD-functionalized tip and are displaced vertically for clarity of presentation. 2D. Histogram (n=110) of pull-off force values for the interaction of QAβ-CD with PLGA nanoparticles and blank substrates obtained with the same tip.

A firm and stable adhesion between the shell-forming material, QAβ-CD, and PLGA nanoparticles added to the overall success of the present platform. Electrostatic interactions between the positively charged quaternary ammonium associated with QAβ-CD and the negatively charged PLGA surface were designed to provide a stable core-shell construct. Therefore, to measure the adhesive force between the component parts, nanoindentation experiments using atomic force microscopy (AFM) were performed employing tips modified with QAβ-CD and a surface covered with PLGA nanoparticles (FIG. 2a). As can be observed in the AFM image comprising FIG. 2b, the substrate was comprehensively overlaid with PLGA nanoparticles. FIG. 2c comprises force-distance curves achieved from pull-off experiments between the QAβ-CD-coated AFM tip and PLGA nanoparticles and control substrates. Following indentation of the PLGA and control surfaces to a desired force value, retraction of the cantilever was examined. The strong adhesion between the tip and the PLGA nanoparticles caused the cantilever to adhere to nanoparticles beyond a certain distance (i), a distance where the tip was successfully separated from control substrates. It was not until after a certain point (ii) that adhesion was broken and the AFM tip was successfully separated from the nanoparticle surface. The average adhesion force between QAβ-CD and PLGA nanoparticles, as determined by force curves in FIG. 2c, was found to be approximately 8.5±0.8 nN (FIG. 2d). In contrast, the adhesion force measured using the same QAβ-CD-functionalized tip and a control surface containing no PLGA nanoparticles was found to be 0.4±0.2 nN.

Force at the single molecule level was estimated using a technique called blind tip evaluation (as described by Yam et al., 2003). The tip diameter was approximated as 8 nm after immersion in QAβ-CD solution, leading to the estimation that on the apex of the tip, 6-8 QAβ-CD molecules were present on the surface. Thus, the maximum force between a single QAβ-CD molecule and PLGA was determined to be 1.1 nN. In contrast, the maximum force between a single QAβ-CD molecule and the control surface was 59.2 pN. The adhesive force between QAβ-CD and PLGA proved extremely strong, especially when compared to biological interactions in nature. Compared with for example, the single molecule force between IgG and single strand DNA which was approximately 50 pN (Zhu, et al., 2010). This strong force between QAβ-CD and the PLGA surface is most likely a combination of ionic, Van der Waals, and molecular interaction forces. The firm adhesion between the core forming material and shell contributed to pronounced stability of the nanoparticle upon intravenous infusion into the blood stream, preventing undesirable premature release of drugs prior to arrival at the tumor site.

Example 3—Nested Nanoparticle Size and Morphology Characterization

Figure 3:
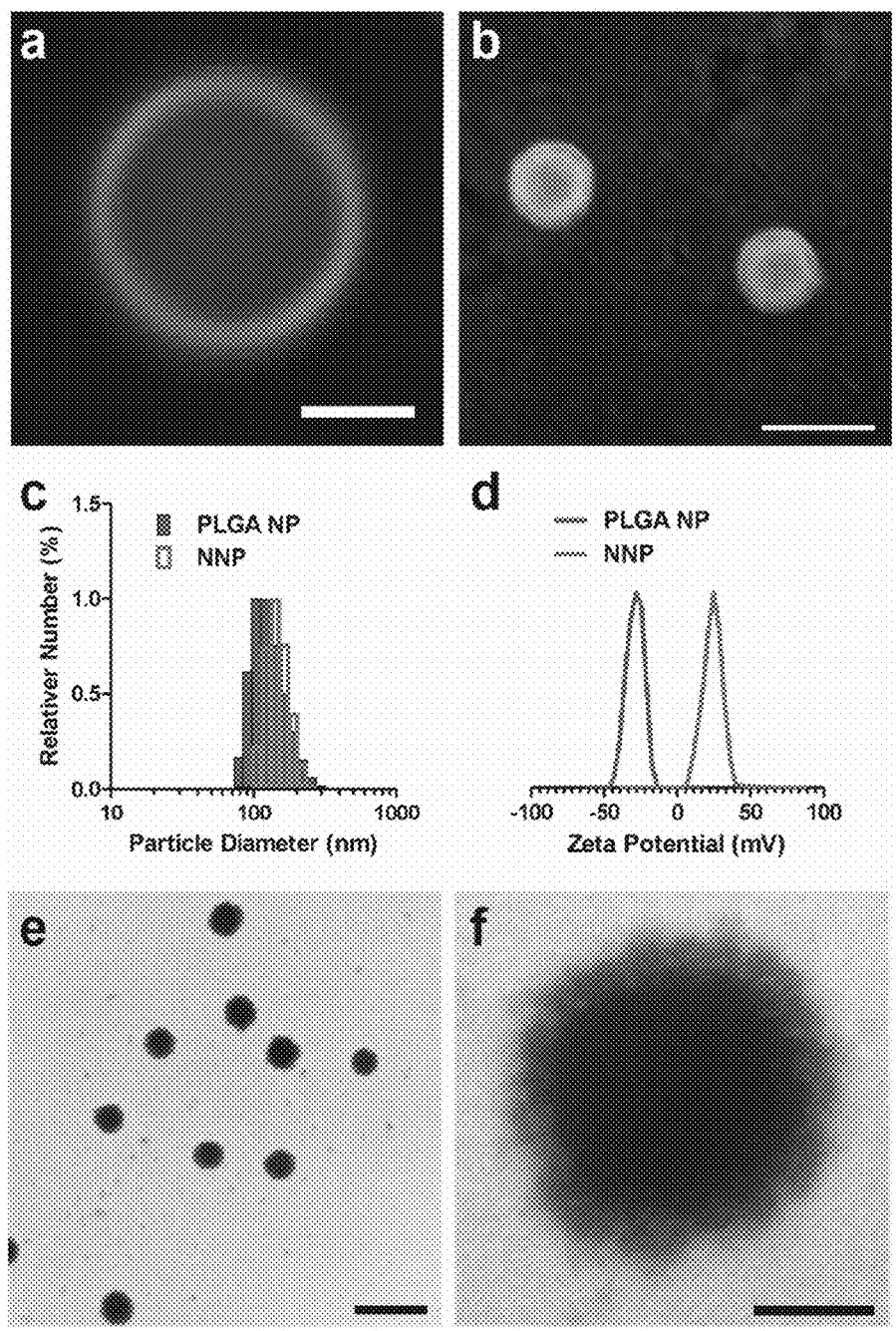
FIGS. 3A-F. Illustrates the characterization of nested nanoparticle. 3A. Confocal microscopy image of a single nested particle demonstrating the core-shell compartmentalization of bodipy and rhodamine. The scale bar represents 5 μm. 3B. Scanning electron microscopy (SEM) micrograph of nested nanoparticles. The scale bar represents 200 nm. 3C. Dynamic light scattering histogram depicting the size of nanoparticles prior to (open bars) and after (filled bars) functionalization with the QAβ-CD shell. 3D. Zeta potential analysis of nanoparticles prior to (right histogram) and after (left histogram) addition of the QAβ-CD shell. 3E. Transmission electron microscopy image of nested nanoparticles. The scale bar represents 500 nm. 3F. Magnification of nested nanoparticle from e. The scale bar represents 100 nm.

Having verified the strong adhesion between core- and shell-forming components, the nested nanoparticle platform, comprising a drug-containing nanoparticle core coated with a shell composed of cyclodextrin-complexed drug (FIG. 3a), was fabricated and characterized. Throughout the entirety of the study, the fluorophores rhodamine and bodipy were used as model drugs for encapsulation within PLGA nanoparticles and complexation with QAβ-CD, respectively. For ease of platform morphological and architectural analysis, specifically core-shell compartmentalization of distinct drugs, rhodamine-containing PLGA microspheres averaging 2 μm in diameter were fabricated and subsequently coated with bodipy-cyclodextrin complexes (bodipy•QAβ-CD). Upon examination of nanoparticles via confocal microscopy, rhodamine (red) encapsulated within the PLGA core and a bodipy•QAβ-CD shell (green) enveloping the nanoparticle were clearly discernible (FIG. 3b). As hypothesized, the outer drug layer formed a dense uniform coating around the nanoparticle, with distinct compartmentalization of the two drugs within the system.

Figure 7:
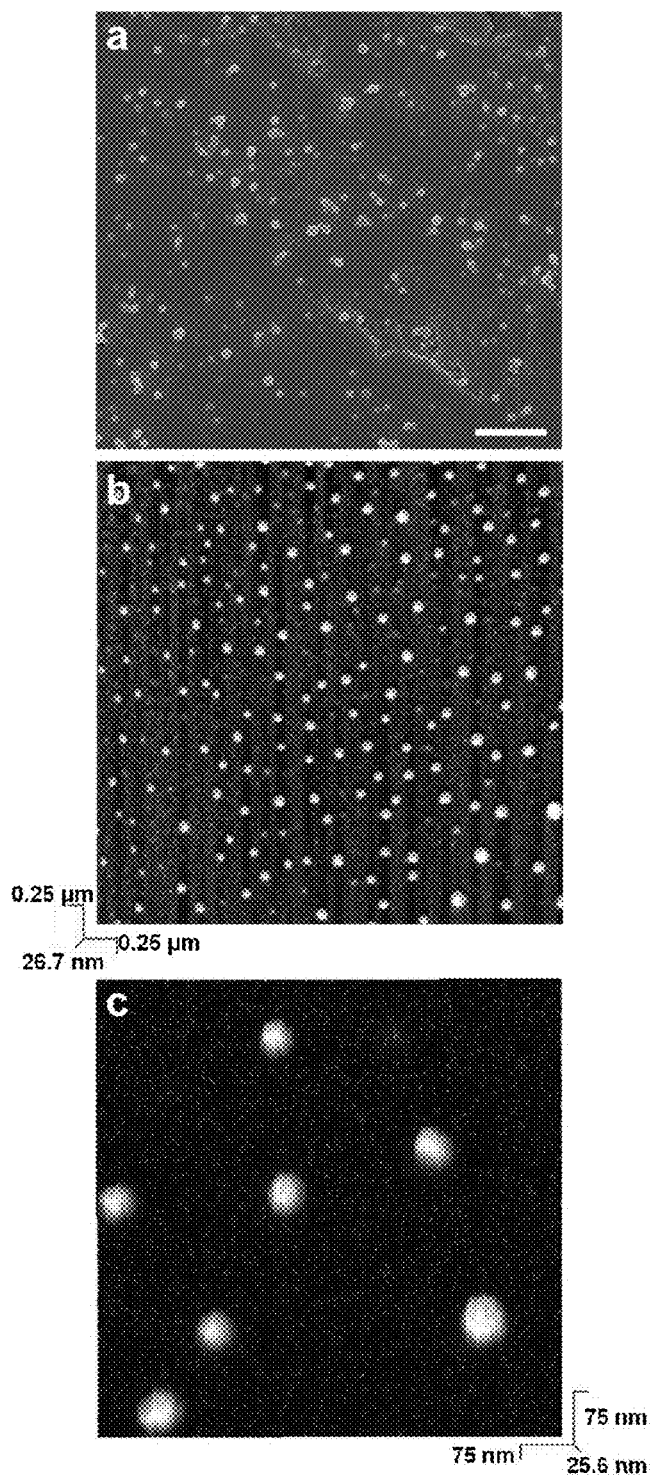
FIGS. 7A-C. Illustrate SEM and AFM examination of nested nanoparticles. 7A. SEM image of nested nanoparticles. The scale bar represents 1 μm. 7B-C. AFM images of nested nanoparticles, with c. comprising a magnification of nanoparticles.
Figure 8:
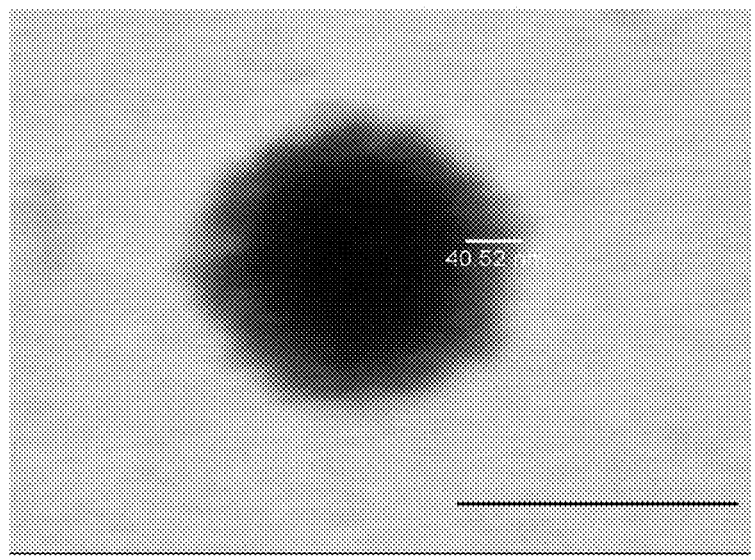
FIG. 8. Illustrates cyclodextrin shell thickness quantification. TEM and ImageJ analysis used to determine the thickness of the cyclodextrin shell surrounding nested nanoparticles, which was found to average 40 nm.

The morphology and architecture achieved on the microscale effectively translated towards the nanoscale, a size range beneficial for both long-term circulation and accumulation in tumors through the EPR effect. Rhodamine-containing PLGA nanoparticles possessed an average diameter of 105 nm as determined by dynamic light scattering (DLS) analysis (FIG. 3c). Upon addition of the bodipy•QAβ-CD outer shell, the size of the nanoparticles increased to an average diameter of 142 nm. SEM and AFM examination demonstrated the small size and spherical morphology of nested nanoparticles, confirming their monodispersity (FIGS. 7a and 7b). Analysis of the surface charge of the nanoparticles, prior to and following addition of the bodipy•QAβ-CD shell, confirmed the presence of the cyclodextrin outer layer. As is evident in FIG. 3d, the negative surface charge associated with PLGA nanoparticles (−28 mV) became highly positive (+25 mV) following the addition of bodipy•QAβ-CD. Successful assembly of the core-shell construct was further verified via TEM, which served to corroborate the small and uniform size of the nanoparticles (FIG. 3e). Magnification of nested nanoparticles under TEM demonstrated the presence of an outer layer surrounding the electron dense mass of the PLGA nanoparticle. Upon subsequent analysis, the thickness of the shell was found to agree with measurements obtained by dynamic light scattering (FIG. 8). Upon phase-separation analysis, the ratio of PLGA:QAβ-CD was found to be approximately 15:1.

Nested Nanoparticle Morphology and Size Characterization Via SEM and AFM:

Nested nanoparticle size and morphology were examined using scanning electron microscopy (SEM) and atomic force microscopy (AFM). As can be seen in FIG. 7, nested nanoparticles were small in diameter, agreeing with the size of the nanoparticles as determined by dynamic light scattering. The SEM and AFM micrographs also depict the spherical shape of the nanoparticles, as well as the monodispersity of the sample.

AFM Tip Functionalization:

AFM non-conductive silicon nitride (Si3N4) tips (Bruker, Camarillo, Calif., USA) were used in all modifications and the same tip used for all experiments. The silicon wafer was sectioned into 0.5×0.5 cm slices and immersed in isopropyl alcohol (IPA). Chemical modifications of AFM tips and substrates for force measurements were carried out following a previously published procedure (Shi et al., 2009). Briefly, tips were initially cleaned and hydroxylated using plasma to generate Si—OH groups. Cleaned tips were gently transferred into a solution of 1% (v/v) MPTMS in IPA/H$_2$O (5% water), incubated for 2 h at RT, and then washed thoroughly with IPA and water. They were then incubated in 1.0 mg/ml QAβ-CD solution for 3 h at RT, and rinsed thoroughly with water. The positively charged QAβ-CD was added to tips though electrostatic interaction. After rinsing with DI water, the modified tips were air-dried in a clean container for subsequent use. For substrate modification, hydroxylated silicon slices were immersed in a 1% (v/v) APTES solution in IPA/H$_2$O (5% water) and incubated at RT for 2 h. PLGA nanoparticles were then settled onto the surface though electrostatic interaction, and after rinsing with DI water, the substrates were dried under a nitrogen stream.

The cantilever used in the measurement was an MLCT cantilever (Bruker Nano Inc.) with a spring constant of 0.03 N/m and a sensitivity of 64 nm/V, with experiments conducted on a MultiMode 8 AFM system (Bruker, Madison, Wis., USA). Force ramp conditions were set at 1 µm for ramp size, 1 Hz for ramp frequency, and a threshold of 2 nm for cantilever deflection (absolute). All measurements were performed at RT.

Nested Nanoparticle QAβ-CD Shell Thickness:

The thickness of the cyclodextrin (QAβ-CD) shell surrounding the nested nanoparticles was examined via transmission electron microscopy (TEM). Briefly, 8 radial measurements of 10 nanoparticles were obtained using ImageJ software. FIG. 8 depicts a magnification of a representative nested nanoparticle, with a radial measurement conducted to determine the thickness of the cyclodextrin coating. The average thickness of the cyclodextrin shell around the nanoparticle was determined to be 40.5±8 nm, well in agreement measurements obtained using dynamic light scattering.

Example 4—Characterization of Release from Nested Nanoparticles

Figure 4:
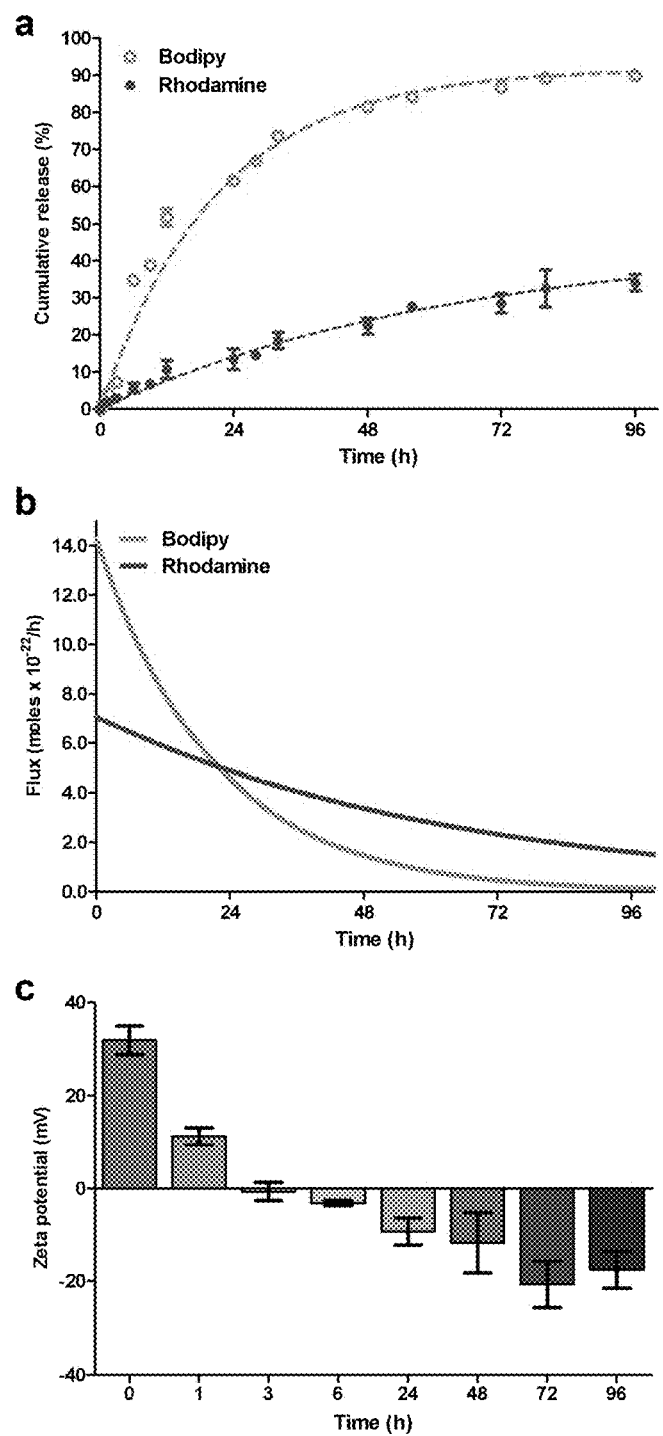
FIGS. 4A-C. Examination of nested nanoparticle release kinetics. 4A. Cumulative release of bodipy (open circles) and rhodamine (filled circles) from nested nanoparticles in PBS at pH 7.4 and 37° C. Model fits to experimental data are represented by dotted lines. 4B. Fluxes of bodipy and rhodamine release from nested nanoparticles. 4C. Zeta potential examination of nested nanoparticles at specific timepoints in simulated release conditions (PBS at pH 7.4 and 37° C.).

FIG. 4 summarizes the release kinetics of rhodamine and bodipy from nested nanoparticles. As is evident in FIG. 4a, minimal drug release occurred from nanoparticles in the initial timepoints leading up to 3 h (7% and 3% of bodipy and rhodamine, respectively). Nominal release at early timepoints following intravenous administration should limit accumulation of drugs in healthy tissues and organs, in turn hindering potential adverse effects, and allowing sufficient time for the nanoparticle to successfully accumulate at the site of action prior to release. After 3 h, an increase in bodipy release occurred, reaching 34% of drug by 6 h. By 12 h, 50% of bodipy was released from nanoparticles, with release plateauing after 48 h. It is important to note that minimal release of rhodamine (~6%) occurred by this same timepoint. Indeed, throughout the entirety of the study, rhodamine release was extremely slow and sustained, reaching merely 34% release in 96 h.

Due to the fact that the physico-chemical properties of the core and shell, as well as bodipy and rhodamine, are different, a computational method accounting for diffusivities and molecule partitioning was used to analyze release kinetics from nested nanoparticles. Use of the model helped determine that sequential release may be achieved and controlled not only by different diffusion properties in different phases, but also partitioning. Modeling results suggest that release from the core and shell saturated at 46% and 92%, respectively. The model estimated experimental release curves by using partitioning coefficients of 5.0×109 and 2.2×1011 for bodipy and rhodamine, respectively (FIG. 4a). The half-time of release of the maximum releasable material was estimated to be 15 h for the shell and 46 h for the core. The diffusivity of rhodamine inside the PLGA nanoparticle matrix was estimated to be $4 \times 10^{-10}$ cm2/s, which was approximately 104 times lower than that in water, while that of bodipy in the shell was reduced by only 5 times compared to that in water. Based on the model fit, the partitioning of both rhodamine and bodipy proved to be the most important factor influencing release kinetics, proving critical in the design of future embodiments of nested nanoparticles for sequential release. This is illustrated in the distinct phases of dominant fluxes over time (FIG. 4b). The rate of release of rhodamine from nested nanoparticles was initially outperformed by bodipy release, but eventually the rhodamine flux overtook the flux of bodipy after 24 h.

Nanoparticle surface charge examination at distinct timepoints provided valuable insights into the mechanism of drug release. As apparent in FIG. 4c, the nested nanoparticle platform was positively charged at the initial timepoints. However, as time progressed, the nanoparticle became less positive, with the surface charge undergoing an inflection and shift towards negative values after the 3 h timepoint. Noticeably, this coincided with the timeframe of increased release of bodipy observed in FIG. 4a. At subsequent times, the nanoparticle became increasingly negative, plateauing at roughly the same time as bodipy release. Taken together, the mechanism of release of bodipy from nested nanoparticles was driven primarily through detachment and displacement of cyclodextrin-complexed drug from nanoparticle surfaces. Partitioning analysis demonstrated preference of rhodamine molecules for the PLGA phase. Confocal microscopy of nested nanoparticles at distinct timepoints also highlighted the mechanism of release. At early timepoints, the nanoparticles were coated by the bodipy•QAβ-CD shell, which dissipated over time, giving way to nanoparticles with a sustained presence of rhodamine within their cores.

Modeling of Release Kinetics:

A Finite Element (FE) method was used to model drug diffusion. The model included partitioning conditions at the surfaces, in this case between the core and the surrounding fluid. Thus, aside from the incremental-iterative system of mass balance equations (Kojic et al., 2008; Ziemys et al., 2011; Kojic et al., 2011):

$$\left(\frac{1}{\Delta t}M + K\right)\Delta C^{(i)} = Q^{ext} - Q^{int(i-1)}$$

the partitioning condition was included $$\Delta N_s / \Delta N_f = \Delta C_s / \Delta C_f = P$$

Here, M and K are element mass and diffusion matrices, $\Delta C$ represents nodal concentration increments, $Q^{ext}$ and $Q^{int}$ are external and internal nodal mass fluxes; $\Delta N_s$ and $\Delta N_f$ are number of molecules of solid and fluid (per FE node) passing during time step $\Delta t$, and $\Delta C_s$ and $\Delta C_f$ are the corresponding concentration changes at boundary nodes with partitioning property; P is partitioning coefficient; and i specifies the equilibrium iteration counter. The important material parameter in the above balance equation is the diffusion coefficient D entering the diffusion matrix K:

$$K_{IJ} = \int_V D(\partial N_I / \partial x_j \partial N_J / \partial x_j) dV$$

where $N_I$, $N_J$ are interpolation functions and V is element volume. This computational procedure was built into the FE package PAK (Kojic et al., 1996).

TABLE 1

The table below shows the parameters used to establish the model:

|  | Core | Shell | Units | Comments |
|---|---|---|---|---|
| R | 52.5 | 70.5 | nm | |
| d | — | 18 | nm | (shell thickness) |
| Mol · Mass | 479 | 661 | Da | |
| $C_{t=0}$ | 0.069 | 0.039 | M | (initial molar concentration) |
| logP | 319 [4] | 0.013 [4] | | (for comparison only: octanol/water) |

TABLE 1-continued

The table below shows the parameters used to establish the model:

| | Core | Shell | Units | Comments |
|---|---|---|---|---|
| $D_{water}$ | $4 \cdot 10^{-6}$ | $4 \cdot 10^{-6}$ | cm$^2$/s | (diffusivity in water) |
| *$D_{NP}$ | $D_{water}/5$ | $D_{water}/10^4$ | cm$^2$/s | (diffusivity inside material) |
| *Partitioning | $5 \cdot 10^9$ | $2.2 \cdot 10^{11}$ | | (between water and solid material) |
| $R^2$ | 0.99 | 0.82 | | (square of Pearson's r between experiment and simulation) |

*values adopted to fit the experimental release.

The core composed of PLGA showed no significant degradation within the timeframe of experiments, and thus, diffusion was assumed to govern release of material. The shell composed of QAβ-CD was assumed to be either lost or degraded within or after a certain period of release, where diffusion of bodipy alone or bodipy complexed with QAβ-CD was estimated to be similar in nature due to small differences of the final molecular size. The experimental diffusivity, $D_{water}$, was established for rhodamine (4.10$^{-6}$ cm$^2$/s) (Galoian et al., 2012), but was approximated for bodipy based on the literature. We also assumed that release from shell and core compartments did not substantially affect one another. Diffusivities inside the material (core and shell) were fitted together with partitioning coefficients P.

Confocal Microscopy Examination of Drug Release from Nested Nanoparticles:

Confocal microscopy was used to obtain a qualitative visualization of drug release from nested nanoparticles in PBS 7.4 at 37° C. At predetermined time-points, nanoparticles were removed from release media and examined using confocal microscopy. Results demonstrate that at short timepoints of 1 h, nanoparticles contained the bodipy•QAβ-CD shell surrounding the core, as evidenced by green fluorescence. At 24 h, the population of nanoparticles containing bodipy decreased, and the rhodamine-containing core became apparent in nanoparticles. At later timepoints of 48 and 96 h, the bodipy cyclodextrin shell became disassociated from the nanoparticles, resulting in rhodamine-containing nanoparticles (red fluorescence).

Figure 10:
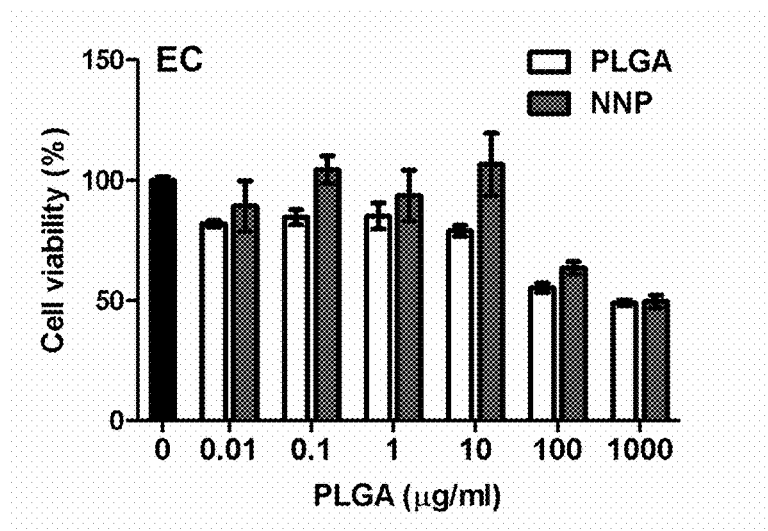
FIG. 10. Illustrates cytotoxic effects of NPP, as determined using a MTT assay, in human primary endothelial cells following 24 h incubation with nested nanoparticles and control PLGA nanoparticles at varying doses.

Example 5—Nested Nanoparticle Internalization and Intracellular Sequential Release within Breast Cancer Cells Potential cytotoxic effects stemming from the nested nanoparticle platform were examined in human primary endothelial cells via MTT assay. Nested nanoparticles did not have a significant detrimental effect on cell viability. As can be seen in FIG. 10, nested nanoparticles overtly cytotoxic over the range of doses examined. Toxicity was absent at low doses, however, cell viability was affected at higher doses, a toxicity likely resulting from PLGA as it correlated directly with that observed with PLGA controls at these same doses.

Figure 5:
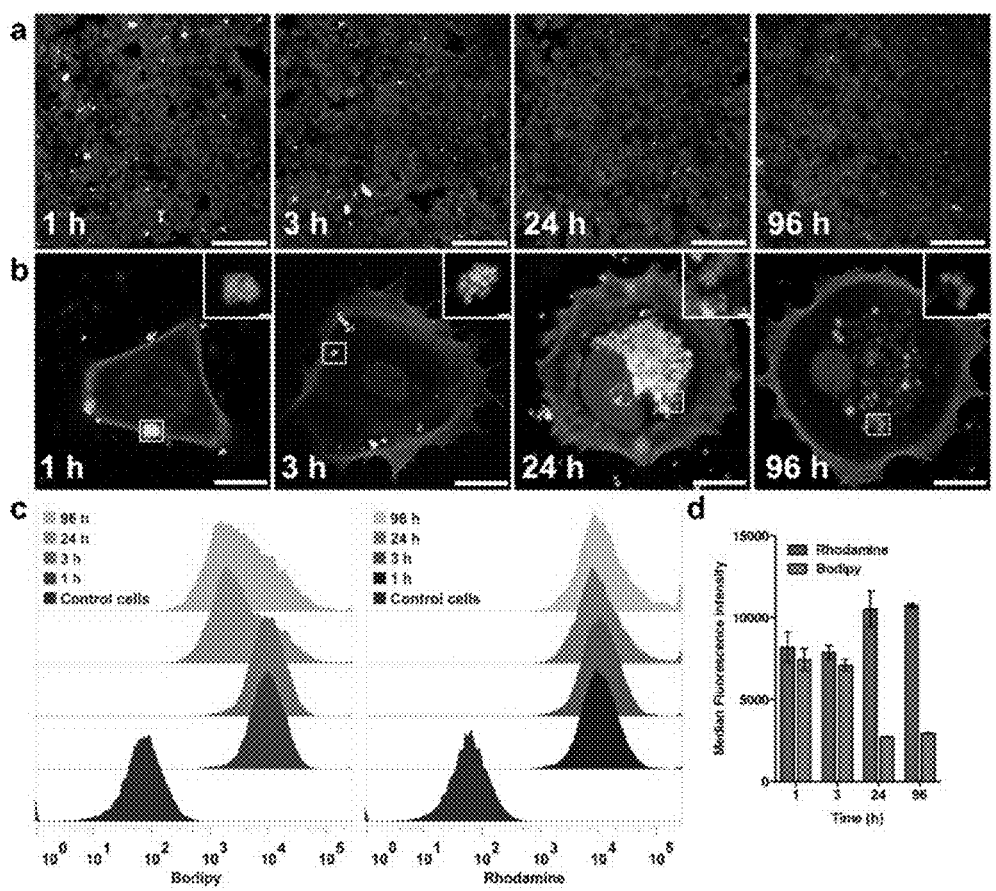
FIGS. 5A-D. Internalization of nested nanoparticles and intracellular release in MCF-7 breast cancer cells. 5A. Confocal microscopy of MCF-7 breast cancer cells at predetermined timepoints after administration of nested nanoparticles. The scale bar represents 100 μm. 5B. Single-cell confocal microscopy examination of nested nanoparticle internalization and release at different timepoints. The scale bar represents 40 μm. Figure insets represent magnifications of areas outlined in boxes. The scale bars in the insets represent 2 μm. 5C. Flow cytometry histograms of nanoparticle accumulation over time in MCF-7 breast cancer cells. 5D. Mean fluorescence intensity over time in MCF-7 breast cancer cells as determined by flow cytometry analysis.

Nanoparticle internalization and subsequent intracellular localization and drug release were examined in MCF-7 breast cancer cells (FIG. 5). As can be observed in confocal micrographs comprising FIG. 5a, nested nanoparticles underwent internalization in MCF-7 breast cancer cells after 1 h of incubation. Internalization of nested nanoparticles was evident. Intracellular release of drugs over time was also evident, with fluorescence of bodipy waning as time progressed past the 3 h timepoint. At later timepoints of 24 and 96 h, the fluourescence emanating from MCF-7 cells was primarily due to rhodamine in nanoparticles, with the majority of bodipy having been released.

Single-cell analysis (FIG. 5b) provided further insights into nested nanoparticle internalization and release, as well as intracellular trafficking. By 1 h, nanoparticles have undergone association with the cell membrane, and were shown to undergo engulfment in early endosomes. At later timepoints, larger amounts of nanoparticles were internalized, leading to the formation of larger, late-stage endosomal compartments. As can be seen at timepoints of 24 and 96 h, migration of nanoparticles to the perinuclear region of the cell has occurred, with nanoparticles likely found within lysosomal bodies. Analogous to FIG. 5a, bodipy and rhodamine were found to be co-localized and associated with nanoparticles at early timepoints, while at later timepoints, only rhodamine fluorescence remained, successfully demonstrating intracellular sequential drug release dynamics using the nested nanoparticle platform.

Intracellular release behavior was quantified utilizing flow cytometry analysis. As shown in FIGS. 5c and 5d, the intracellular fluorescence intensity of bodipy decreased significantly after 24 h, confirming the sequential release behavior of the nanoparticles. Contrastingly, and in agreement with in vitro and cellular studies, the release of rhodamine did not vary significantly over time, demonstrating slow and sustained release dynamics.

Figure 9:
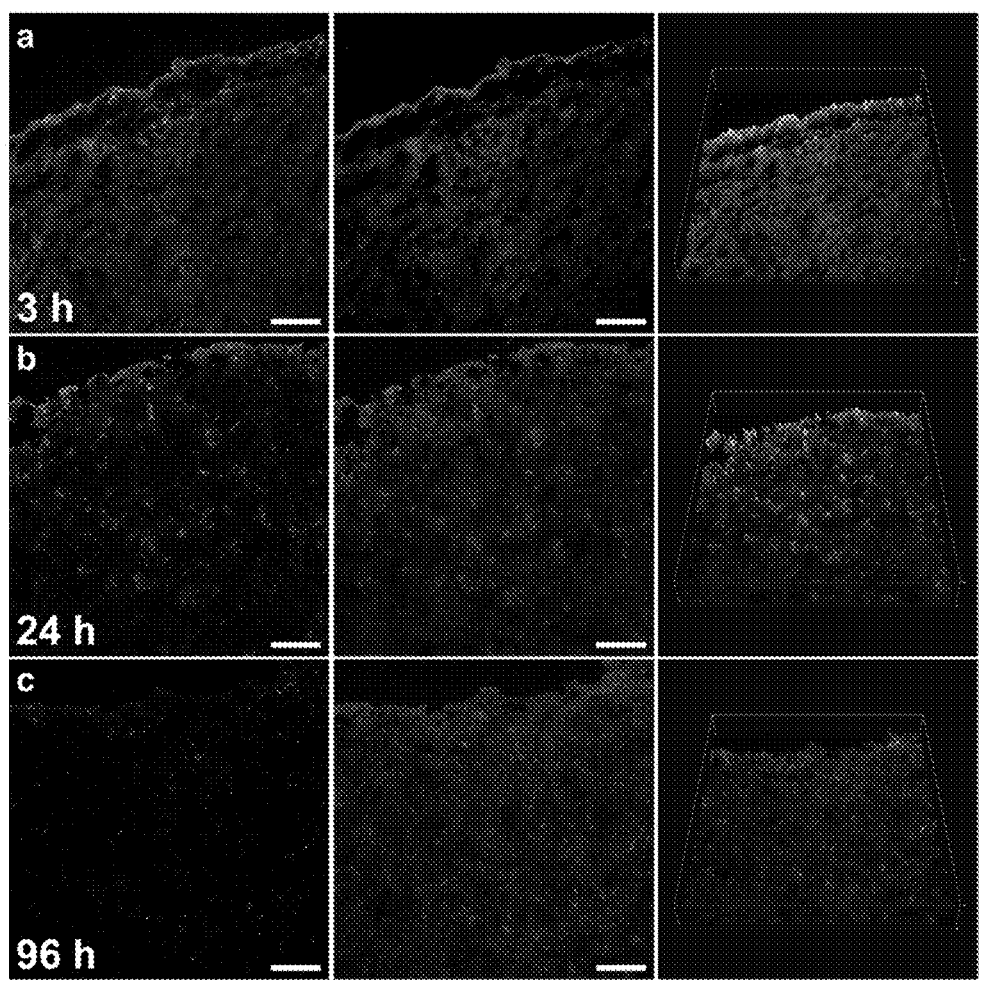
FIGS. 9A-C. Illustrates confocal microscopy examination of MCF-7 tumors following administration of nested nanoparticles. a., b., and c. comprise representative confocal micrographs of tumors at timepoints of 3, 24, and 96 h, respectively. The first column represents detection of the emission spectrum of bodipy when excited with a 640 nm laser, while the second column represents the channel filtered to gather fluorescence emission from rhodamine excited with a laser at 561 nm. The third column to the right represents the digital merger of the fluorescence intensity plots of the two fluorophores.

In Vivo Examination of Sequential Release from Nested Nanoparticles in Murine Models of Breast Cancer:

Following intravenous administration of nested nanoparticles, tumors were excised from mice and fluorescence corresponding to bodipy and rhodamine release from nested nanoparticles examined via confocal microscopy. FIG. 9 demonstrates the intratumoral accumulation of nested nanoparticles at different timepoints. As can be observed in the figure, bodipy signal decreased over time, indicating release during the first 24 hours. In contrast, rhodamine signal remained visible after 96 hours, confirming the slow and sustained release of the agent over time. Fluorescence of bodipy and rhodamine at different timepoints was examined in merged images, yielding co-localization at early timepoints and disassociation of the two agents at later timepoints, highlighting sequential release from nested nanoparticles.

Example 6—Sequential Release from Nested Nanoparticles In Vivo

Figure 6:
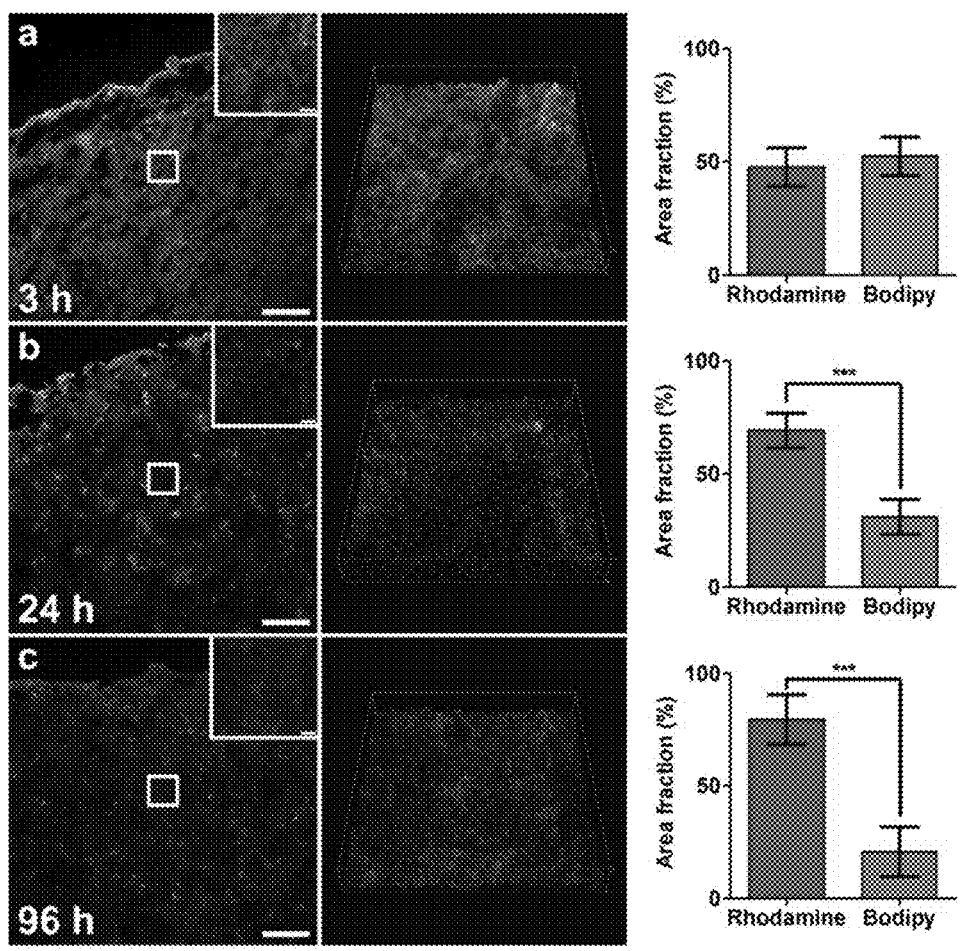
FIGS. 6A-C. Illustrate that nested nanoparticle accumulate, in an MCF-7 murine model of breast cancer. 6A-C comprise representative confocal microscopy images of excised MCF-7 tumors at 3, 24, and 96 h, respectively. Green fluorescence is due to bodipy while red fluorescence denotes the presence of rhodamine. The scale bars in the images represent 100 μm. Immediately to the right of each confocal microscopy image is a fluorescence intensity plot of boxed areas in the preceding figure. The last column of the figure represents area of bodipy and rhodamine as a fraction of the total area, plotted as the percentage of fluorophore content in tumors (n=3), obtained from multiple tissue slices at their corresponding timepoints. Asterisks (***) indicate a significance level of p<0.001.

Nested nanoparticles were designed to successfully navigate the bloodstream following intravenous administration and site-specifically accumulate in tumors, releasing its contents in a time- and sequence-dependent fashion (FIG. 1). MCF-7 breast tumor xenografts from mice were examined for the presence of bodipy and rhodamine using confocal microscopy at different timepoints following administration. As can be seen in FIG. 6a, tumor tissues show colocalization of both dyes 3 h after administration of nested nanoparticles. Surface intensity plots (FIG. 6a, FIG. 9) clearly highlight bodipy and rhodamine fluorescence, indicating accumulation of nanoparticles within the tumor at this relatively short timepoint. Importantly, these findings reinforce the stability of the nanoparticle construct following intravenous administration. Area fraction analysis of distinct regions of the tumor demonstrated that bodipy and rhodamine were found in ratiometrically similar amounts within the tumor at 3 h. In contrast, at 24 h, there was a marked decrease of bodipy in the tumor tissue (FIG. 6b), as reflected in the accompanying surface intensity plot and area fraction analysis. At 96 h, confocal micrographs show that the vast majority of the tumor tissue examined emanated rhodamine-associated fluorescence, with minimal bodipy fluorescence in the tumor (FIG. 6c). Area fraction analysis demonstrated an increase in rhodamine amount at this time in the tumor, while the amount of bodipy in the tumor has decreased significantly. Taken together, these results demonstrate that the nested nanoparticle platform is capable of sequential release intratumorally. Importantly, the slow intratumoral release of drug from the nanoparticle core observed in these studies can provide prolonged exposure to therapeutics.

Figure 11:
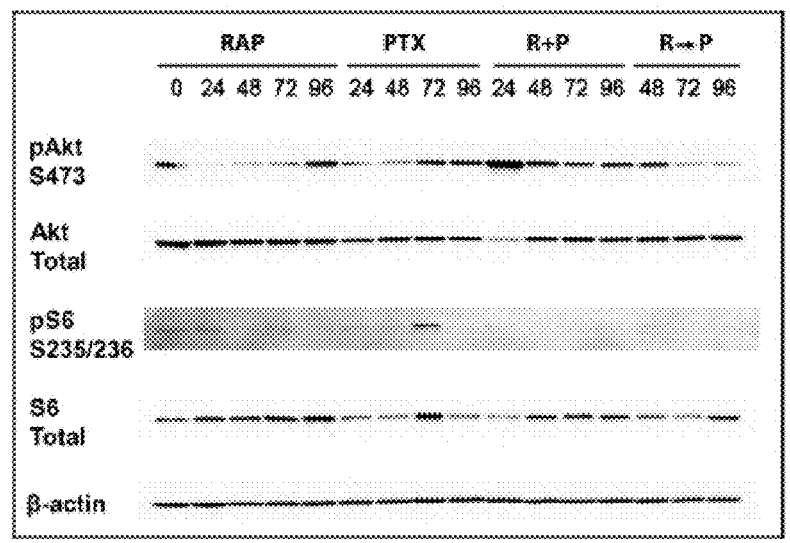
FIG. 11. Time-staggered, sequential administration of rapamycin and paclitaxel to SUM159 breast cancer cells results in efficacious synergistic enhancement compared to concomitant therapy due to suppression of the PI3k/Akt/mTOR pathway. Following simultaneous delivery of low dose rapamycin (0.1 nM) and paclitaxel (1 nM), feedback activation of Akt can be observed over the course of 96 hours. However, following sequential administration of drugs (i.e. rapamycin given 24 hours prior to paclitaxel), activated Akt levels are reduced to below basal levels. Importantly, activated levels of S6, a necessary driver of protein translation, are also reduced.
Figure 12:
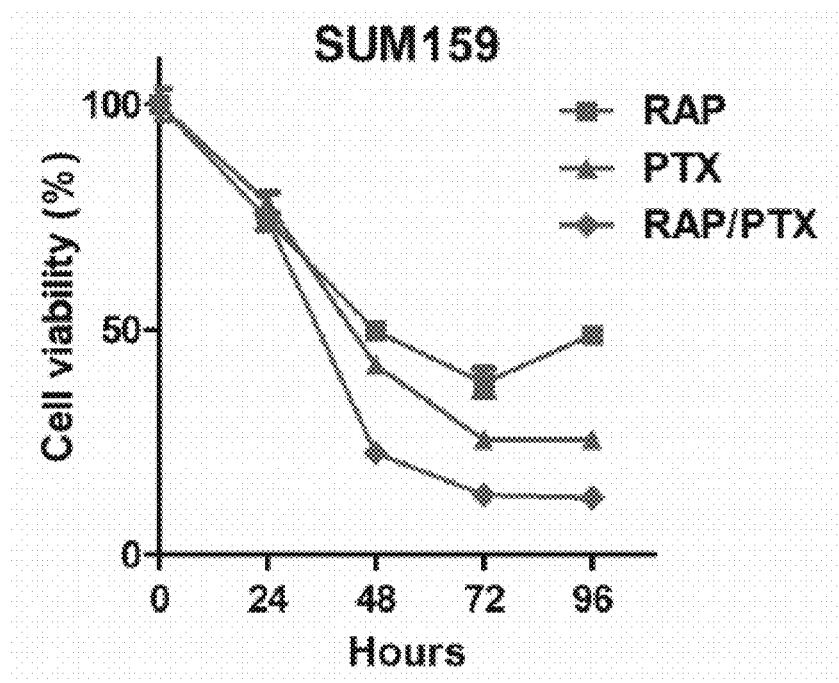
FIG. 12. Rapamycin and paclitaxel, delivered in a time- and sequence-specific fashion, synergistically inhibit breast cancer cell growth. MTT assays of SUM159 breast cancer cells following administration of paclitaxel, rapamycin, and rapamycin followed by paclitaxel 24 hours later (R/P).

Example 7—Examination of Rapamycin and Paclitaxel within the Nested, Nanoparticle Platform The drug rapamycin and chemotherapeutic paclitaxel were shown to act synergistically when delivered in a time and sequential fashion (FIGS. 11 and 12). In this study, rapamycin and paclitaxel were incorporated within nested nanoparticles and used for treatment of triple negative breast cancer.

Figure 13:
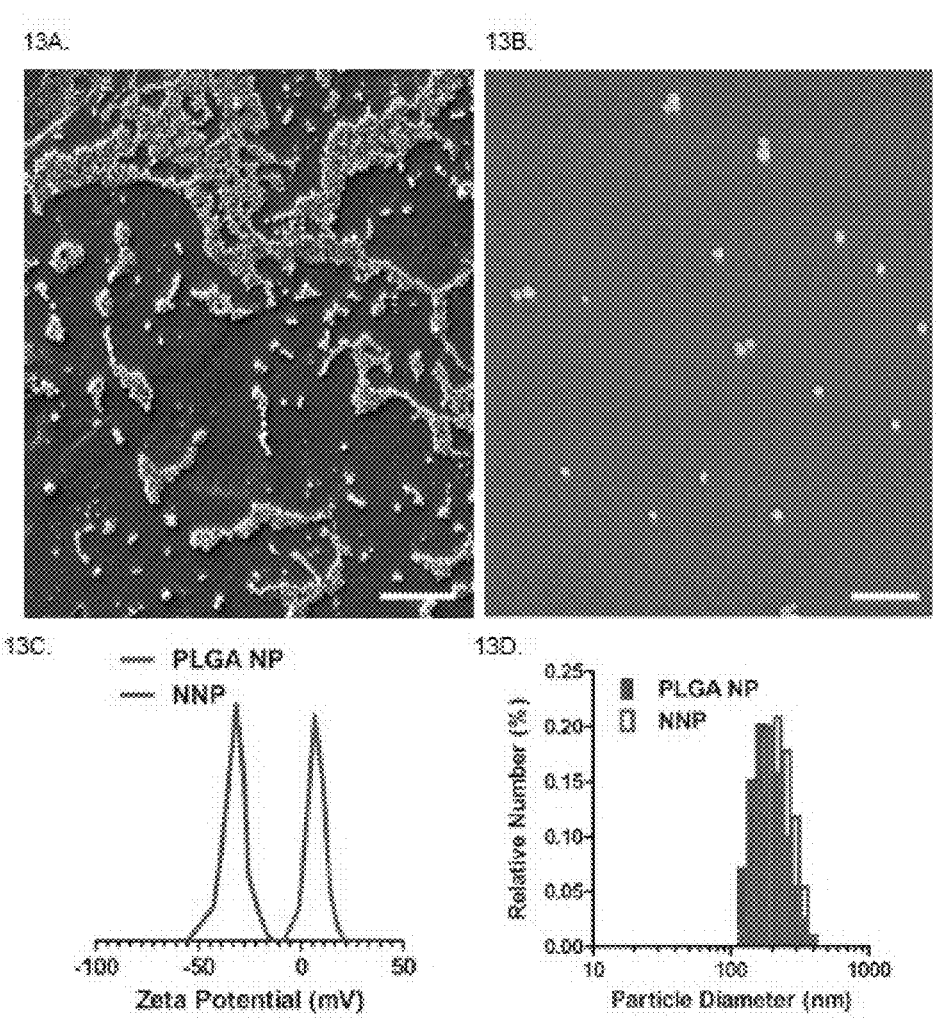
FIGS. 13A-D. Nested nanoparticles, containing rapamycin in the outer shell and paclitaxel within the polymeric core, are small in size and monodisperse. Scanning electron microscopy demonstrates the monodisperse, spherical small size of the nested nanoparticles (13A-B). Resulting nested nanoparticles are slightly positive, measuring ~150 nm as verified by dynamic light scattering (13C-D).
Figure 14:
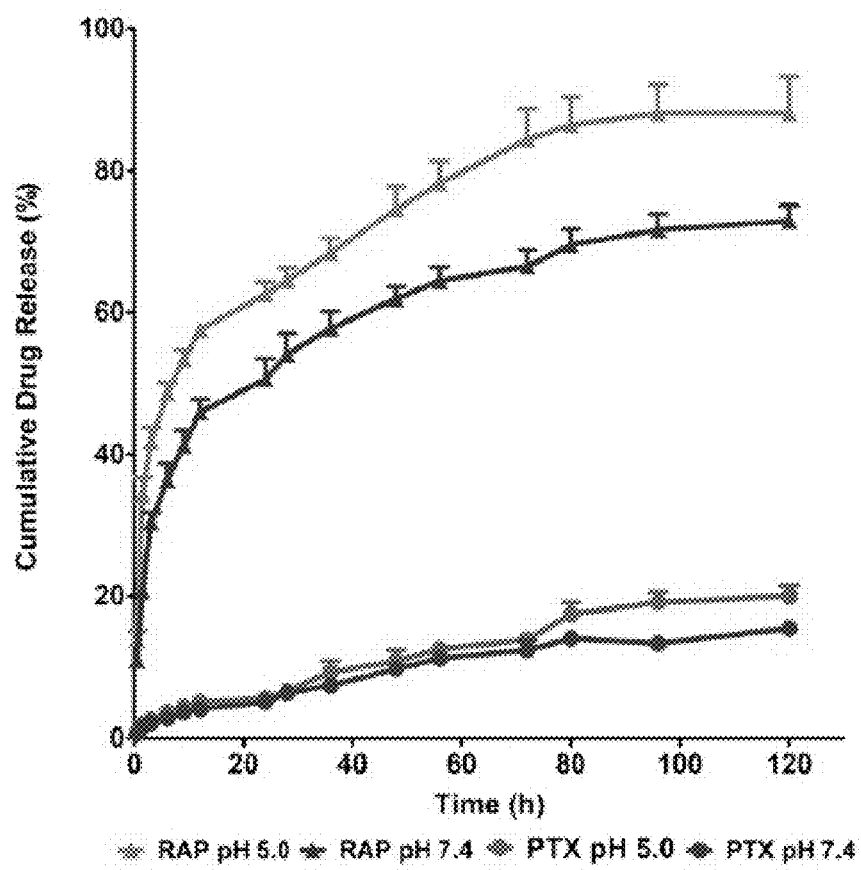
FIG. 14. Nested nanoparticles containing both rapamycin and paclitaxel release drug in a time and sequential fashion. Rapamycin, incorporated within the outer shell of nested nanoparticles, was released rapidly and prior to paclitaxel, which in turn was incorporated within the polymeric core, resulting in a slow and prolonged release.
Figure 15:
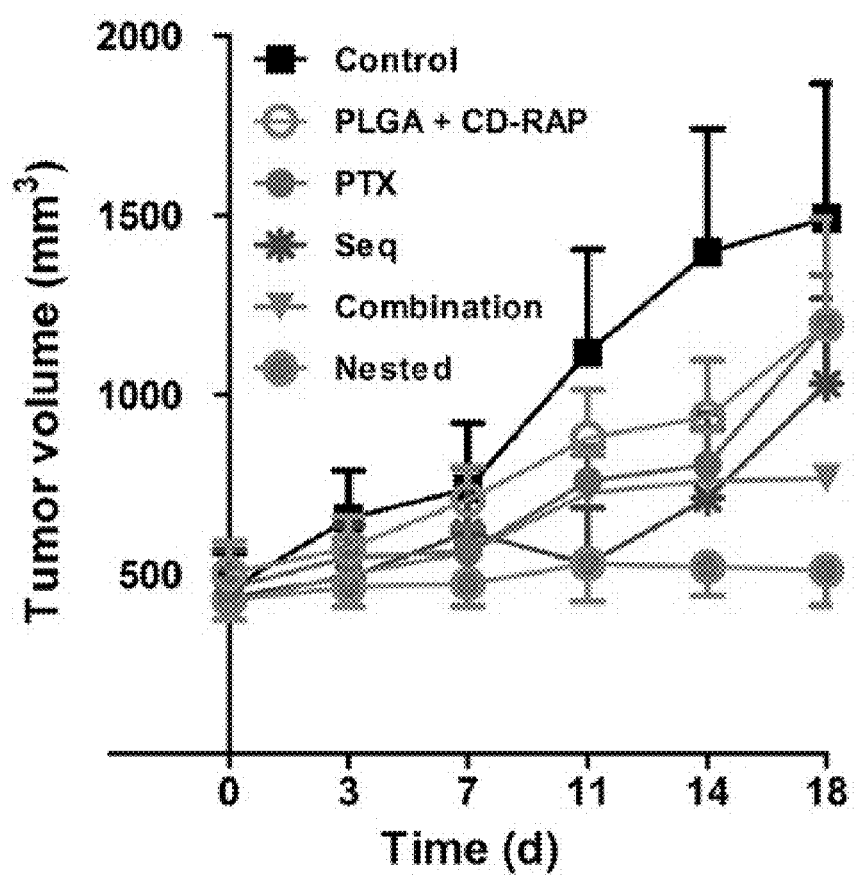
FIG. 15. Nested nanoparticles containing rapamycin in the outer shell and paclitaxel within the polymeric core inhibit triple negative breast cancer growth in mice. Female nude mice, bearing SUM159 breast tumors implanted orthotopically in the mammary fat pad, were administered nested nanoparticles intravenously once a week, resulting in tumor growth inhibition compared to controls that included combined administration of drugs.

Scanning electron microscopy was used to demonstrate the monodisperse, spherical small size of the nested nanoparticles (see FIGS. 13A-B). The nested nanoparticles were slightly positive, measuring ~150 nm as verified by dynamic light scattering (see FIGS. 13C-D). Rapamycin, incorporated within the outer shell of nested nanoparticles, was released rapidly and prior to paclitaxel, which in turn was incorporated within the polymeric core, resulting in a slow and prolonged release (FIG. 14). Female nude mice, bearing SUM159 breast tumors implanted orthotopically in the mammary fat pad, were administered nested nanoparticles intravenously once a week, resulting in tumor growth inhibition compared to controls that included combined administration of drugs (see FIG. 15).

Example 8—Examination of Amiodarone within the Nested, Nanoparticle Platform

The anti-arrhythmic drug, amiodarone, was incorporated in the outer shell and within the polymeric core of nested nanoparticles, so as to obtain an immediate effect of drug followed by a sustained, long-term effect in patients following intrapericardial administration of the platform for the treatment of arrhythmias.

Figure 16:
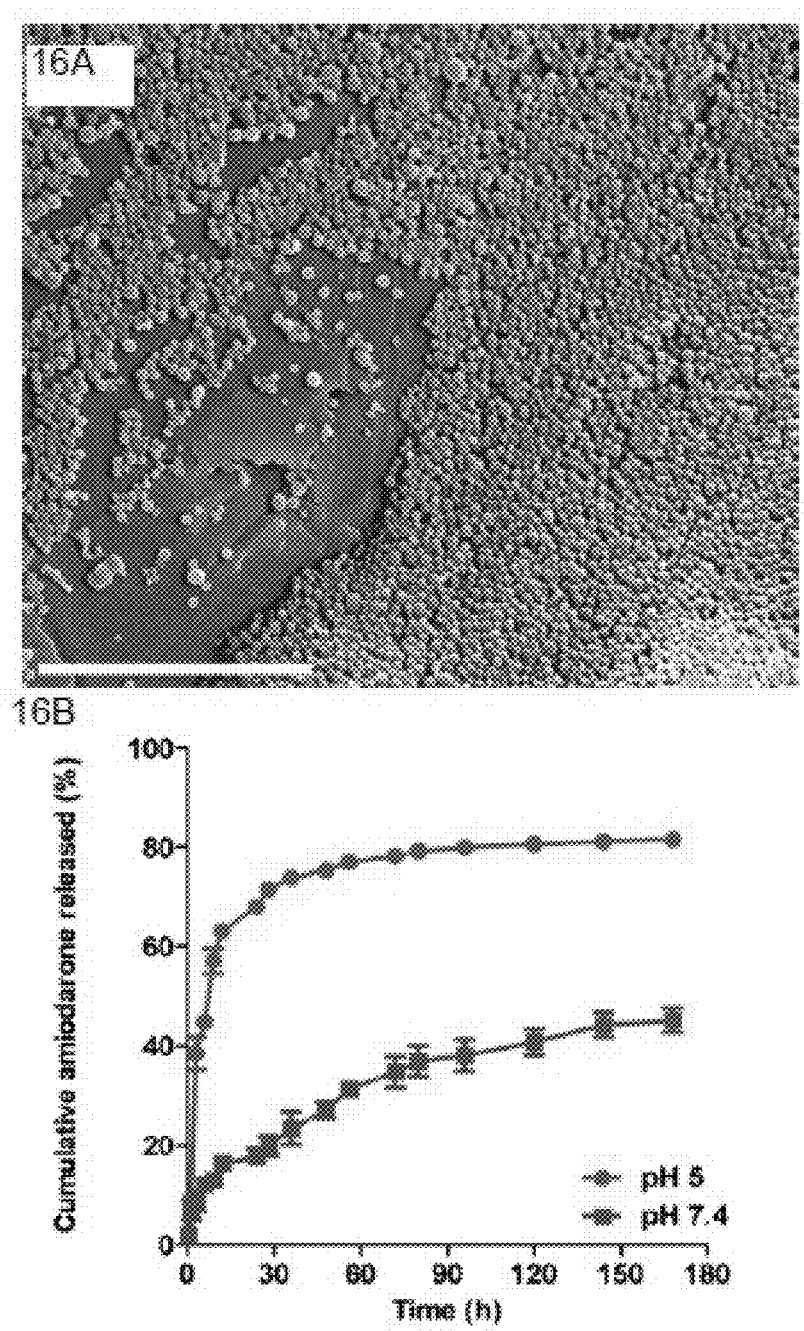
FIGS. 16A-B. Nested nanoparticles containing the anti-arrhythmic drug amiodarone are small in size and display dual burst and sustained release kinetics. Scanning electron microscopy images demonstrate the nanoscale size and monodispersity of the nested nanoparticles (16A). Release kinetics demonstrates the combination of burst and sustained release of amiodarone, ideal for immediate treatment followed by prolonged therapeutic effects (16B).

Nested nanoparticles containing the anti-arrhythmic drug amiodarone were small in size and displayed dual burst and sustained release kinetics. Scanning electron microscopy images demonstrated the nanoscale size and monodispersity of the nested nanoparticles (FIG. 16A). Release kinetics demonstrated the combination of burst and sustained release of amiodarone, ideal for immediate treatment followed by prolonged therapeutic effects (FIG. 16B).

Figure 17:
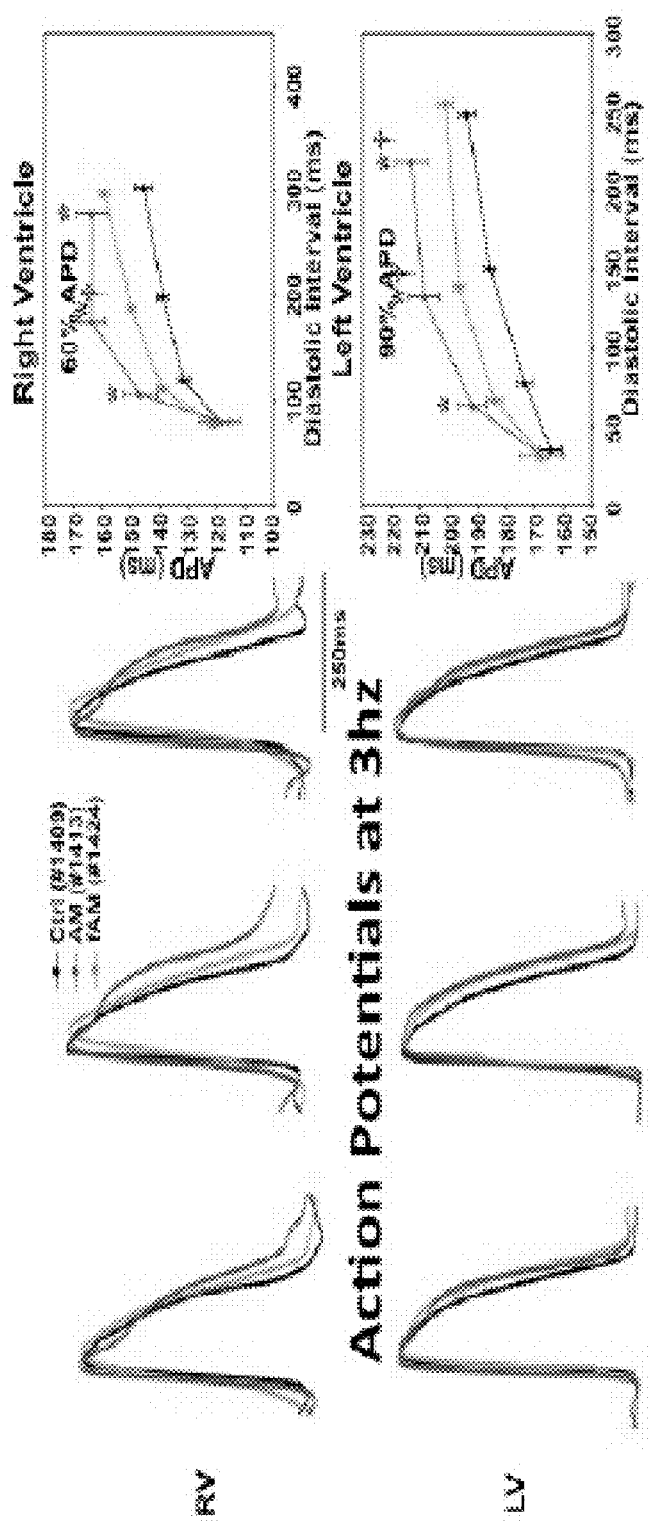
FIG. 17. Nested nanoparticles containing amiodarone administered intrapericardially to rabbits demonstrate prolonged therapeutic effects. Rabbits underwent intrapericardial injection of nested nanoparticles or free amiodarone and were survived for 1 week before undergoing optical mapping. Action potential duration (APD) was prolonged in hearts that received nested nanoparticles compared to untreated controls and rabbits receiving free drug.

As shown in FIG. 17, nested nanoparticles containing amiodarone administered intrapericardially to rabbits demonstrated prolonged therapeutic effects. Rabbits underwent intrapericardial injection of nested nanoparticles or free amiodarone and were survived for 1 week before undergoing optical mapping. Action potential duration (APD) was prolonged in hearts that received nested nanoparticles compared to untreated controls and rabbits receiving free drug.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.
U.S. Pat. No. 4,680,338
U.S. Pat. No. 5,141,648
U.S. Pat. No. 5,563,250
U.S. Pat. No. 5,856,456
Gupta et al., 2005
Ferrari et al., 2005
Shi et al., Exp Cell Res 315, 2847, 2009
Kojic et al., Faculty of Mechanical Engineering University of Kragujevac, Yugoslavia 1996.
Kojic et al., *Computer modeling in bioengineering*: Theoretical background, examples and software, 195, 2008.
Kojic et al., *Journal of the Serbian Society for Computational Mechanics* 5, 104, 2011.
Ziemys et al., *Journal of Computational Physics* 2011.
Galoian et al., Tumour biology: the journal of the International Society for Oncodevelopmental Biology and Medicine 33, 885, 2012.
Yam et al., *J Am Chem Soc* 125, 7498, 2003.
Zhu, et al., *Nat Nanotechnol* 5, 788, 2010.
Stigliano et al., *Molecular pharmaceutics* 10, 3186, 2013.
Woodrow et al., *Nat Mater* 2009, 8, 526.

What is claimed is:

1. A particle comprising (i) a charged poly(DL-lactide-co-glycolide) (PLGA) core element and a first active agent embedded in, or conjugated to, the core element; and (ii) a cyclodextrin coating, surrounding the core element, said coating having the opposite charge of the core element and comprising a second active agent.

2. The particle of claim 1, wherein the first active agent or the second active agent is an imaging agent.

3. A composition comprising a population of particles in accordance with claim 1.

4. The particle of claim 1, wherein the first active agent or the second active agent is a therapeutic agent.

5. The particle of claim 4, wherein the first active agent and the second active agent are therapeutic agents.

6. The particle of claim 5, wherein the first active agent and the second active agent are different therapeutic agents.

7. The particle of claim 5, wherein the first active agent and the second active agent are the same therapeutic agents.

8. The particle of claim 5, wherein the second active agent is an Akt kinase inhibitor and the first active agent is a mechanistic target of rapamycin kinase (mTOR) inhibitor.

9. The particle of claim 8, wherein the Akt inhibitor comprises Paclitaxel or MK-2206.

10. The particle of claim 8, wherein the mTOR inhibitor comprises Rapamycin.

11. The particle of claim 5, wherein the first active agent or the second active agent is an anti-arrhythmic agent.

12. The particle of claim 11, wherein the first active agent and the second active agent are anti-arrhythmic agents.

13. The particle of claim 11, wherein the anti-arrhythmic agent comprises amiodarone.

14. The particle of claim 5, wherein the second active agent is an antibody and the first active agent is a chemotherapeutic.

15. The particle of claim 5, the second active agent is an extracellular signal-regulated kinase (ERK) inhibitor and the first active agent is a rapidly accelerated fibrosarcoma kinase (RAF) inhibitor.

16. The particle of claim 15, wherein the ERK inhibitor comprises SCH772984.

17. The particle of claim 15, wherein the RAF inhibitor comprises GDC-0879.

18. The particle of claim 5, wherein the first active agent is a chemotherapeutic and the second active agent is a drug efflux pump inhibitor.

19. The particle of claim 18, wherein the drug efflux pump inhibitor is P-glycoprotein 1 (P-gP) inhibitor.

20. The particle of claim 19, wherein the P-gP inhibitor comprises Verapamil.

21. The particle of claim 18, wherein the chemotherapeutic comprises doxorubicin or paclitaxel.

22. A method of treating a subject comprising administering a population of particles according to claim 1 to a subject in need of the treatment.

23. A particle comprising a negatively charged PLGA core element having a first active agent embedded therein and a positively charged cyclodextrin coating surrounding the core element, said coating comprising a second active agent.

* * * * *

UNITED STATES PATENT AND TRADEMARK OFFICE
CERTIFICATE OF CORRECTION

| | |
|---|---|
| PATENT NO. | : 10,076,509 B2 |
| APPLICATION NO. | : 15/144340 |
| DATED | : September 18, 2018 |
| INVENTOR(S) | : Elvin Blanco |

It is certified that error appears in the above-identified patent and that said Letters Patent is hereby corrected as shown below:

On the Title Page

Item (54), delete "DELVERY" and insert --DELIVERY-- therefor.

In the Claims

In Claim 15, Column 27, Line 10, after "claim 5," insert --wherein--.

Signed and Sealed this
Twenty-second Day of January, 2019

Andrei Iancu
*Director of the United States Patent and Trademark Office*